United States Patent
Imamura et al.

(10) Patent No.: US 10,310,219 B2
(45) Date of Patent: Jun. 4, 2019

(54) IMAGING APPARATUS, IMAGING SYSTEM THAT INCLUDES IMAGING APPARATUS, ELECTRON MIRROR SYSTEM THAT INCLUDES IMAGING APPARATUS, AND RANGING APPARATUS THAT INCLUDES IMAGING APPARATUS

(71) Applicant: Panasonic Intellectual Property Management Co., Ltd., Osaka (JP)

(72) Inventors: Norihiro Imamura, Osaka (JP); Michihiro Yamagata, Osaka (JP); Tsuguhiro Korenaga, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 624 days.

(21) Appl. No.: 14/680,485

(22) Filed: Apr. 7, 2015

(65) Prior Publication Data

US 2015/0212294 A1 Jul. 30, 2015

Related U.S. Application Data

(63) Continuation of application No. PCT/JP2014/003607, filed on Jul. 8, 2014.

(30) Foreign Application Priority Data

Jul. 30, 2013 (JP) .................................. 2013-157333
Dec. 13, 2013 (JP) .................................. 2013-258388

(51) Int. Cl.
*H04N 5/225* (2006.01)
*G02B 13/00* (2006.01)
(Continued)

(52) U.S. Cl.
CPC ........ *G02B 13/0015* (2013.01); *A61B 5/0077* (2013.01); *G02B 3/005* (2013.01);
(Continued)

(58) Field of Classification Search
CPC .................................................... H04N 5/2254
(Continued)

(56) References Cited

U.S. PATENT DOCUMENTS 5,841,538 A * 11/1998 Schoeffler .............. B64D 15/20
340/583
6,014,413 A * 1/2000 Golden ................ H04B 7/0851
333/18
(Continued)

FOREIGN PATENT DOCUMENTS

JP 2008-010773 1/2008
JP 2008-015157 1/2008
(Continued)

OTHER PUBLICATIONS

International Search Report of PCT application No. PCT/JP2014/003607 dated Oct. 21, 2014.

*Primary Examiner* — Joel W Fosselman
(74) *Attorney, Agent, or Firm* — McDermott Will & Emery LLP

(57) ABSTRACT

An imaging apparatus includes a lens optical system, a color image sensor that includes at least first pixels and second pixels, and a first optical element array disposed between the lens optical system and the color image sensor. In the imaging apparatus, the lens optical system includes optical regions, and the optical regions include a first optical region and a second optical region that differ in terms of at least one selected from the group of spectral transmittance characteristics and transmissive polarization characteristics. The first pixels include respective spectral filters having mutually (Continued)

different spectral transmittance characteristics, and the second pixels include respective spectral filters having at least one type of spectral transmittance characteristics. The first optical element array directs light that has passed through the first optical region to the first pixels and directs light that has passed through the second optical region to the second pixels.

22 Claims, 16 Drawing Sheets

(51) Int. Cl.
| | |
|---|---|
| G03B 13/36 | (2006.01) |
| G03B 15/00 | (2006.01) |
| A61B 5/00 | (2006.01) |
| G02B 3/00 | (2006.01) |
| G02B 5/20 | (2006.01) |
| H04N 5/232 | (2006.01) |
| H04N 5/369 | (2011.01) |
| H04N 9/04 | (2006.01) |
| H04N 13/02 | (2006.01) |

(52) U.S. Cl.
CPC ............ *G02B 5/20* (2013.01); *G03B 13/36* (2013.01); *G03B 15/00* (2013.01); *H04N 5/2254* (2013.01); *H04N 5/23212* (2013.01); *H04N 5/3696* (2013.01); *H04N 9/045* (2013.01); *A61B 2562/0233* (2013.01); *A61B 2562/066* (2013.01); *H04N 5/23219* (2013.01); *H04N 13/0217* (2013.01)

(58) Field of Classification Search
USPC ........................................................ 348/345
See application file for complete search history.

(56) References Cited

U.S. PATENT DOCUMENTS

| | | | | |
|---|---|---|---|---|
| 6,415,141 B1* | 7/2002 | Kakura | ............... | H04B 7/0805 |
| | | | | 375/347 |
| 6,611,243 B1* | 8/2003 | Moseley | ............ | G02B 27/2214 |
| | | | | 345/4 |
| 7,433,042 B1 | 10/2008 | Cavanaugh et al. | | |
| 2004/0207810 A1* | 10/2004 | Nishihira | ................. | A61H 5/00 |
| | | | | 351/200 |
| 2008/0011937 A1 | 1/2008 | Toshikiyo | | |
| 2009/0315993 A1 | 12/2009 | Hirai | | |
| 2010/0231546 A1 | 9/2010 | Digon | | |
| 2011/0169912 A1* | 7/2011 | Abe | .................... | G02B 13/0045 |
| | | | | 348/36 |
| 2012/0002018 A1 | 1/2012 | Hiramoto et al. | | |
| 2012/0002042 A1* | 1/2012 | Okuma | ..................... | A61J 7/02 |
| | | | | 348/135 |
| 2012/0182438 A1 | 7/2012 | Berkner et al. | | |
| 2012/0268643 A1 | 10/2012 | Imamura | | |
| 2013/0063569 A1 | 3/2013 | Sato et al. | | |
| 2013/0070146 A1 | 3/2013 | Imamura | | |
| 2013/0123985 A1* | 5/2013 | Hirai | ..................... | G01N 21/21 |
| | | | | 700/259 |
| 2013/0135453 A1 | 5/2013 | Kanamori | | |
| 2013/0182169 A1 | 7/2013 | Kosugi et al. | | |
| 2013/0188051 A1* | 7/2013 | Ishigaki | ............. | G06K 9/00825 |
| | | | | 348/148 |
| 2013/0215237 A1* | 8/2013 | Inoue | ................... | H04N 13/025 |
| | | | | 348/49 |

FOREIGN PATENT DOCUMENTS

| | | |
|---|---|---|
| JP | 2008-237243 | 10/2008 |
| JP | 2010-025915 | 2/2010 |
| JP | 2011-505045 | 2/2011 |
| JP | 2011-097987 | 5/2011 |
| JP | 2012-150112 | 8/2012 |
| JP | 2012-247645 | 12/2012 |
| JP | 2013-106189 | 5/2013 |
| WO | 2011/083543 | 7/2011 |
| WO | 2011/148851 | 12/2011 |
| WO | 2012/039086 | 3/2012 |
| WO | 2012/120584 | 9/2012 |
| WO | 2012/143983 | 10/2012 |

* cited by examiner

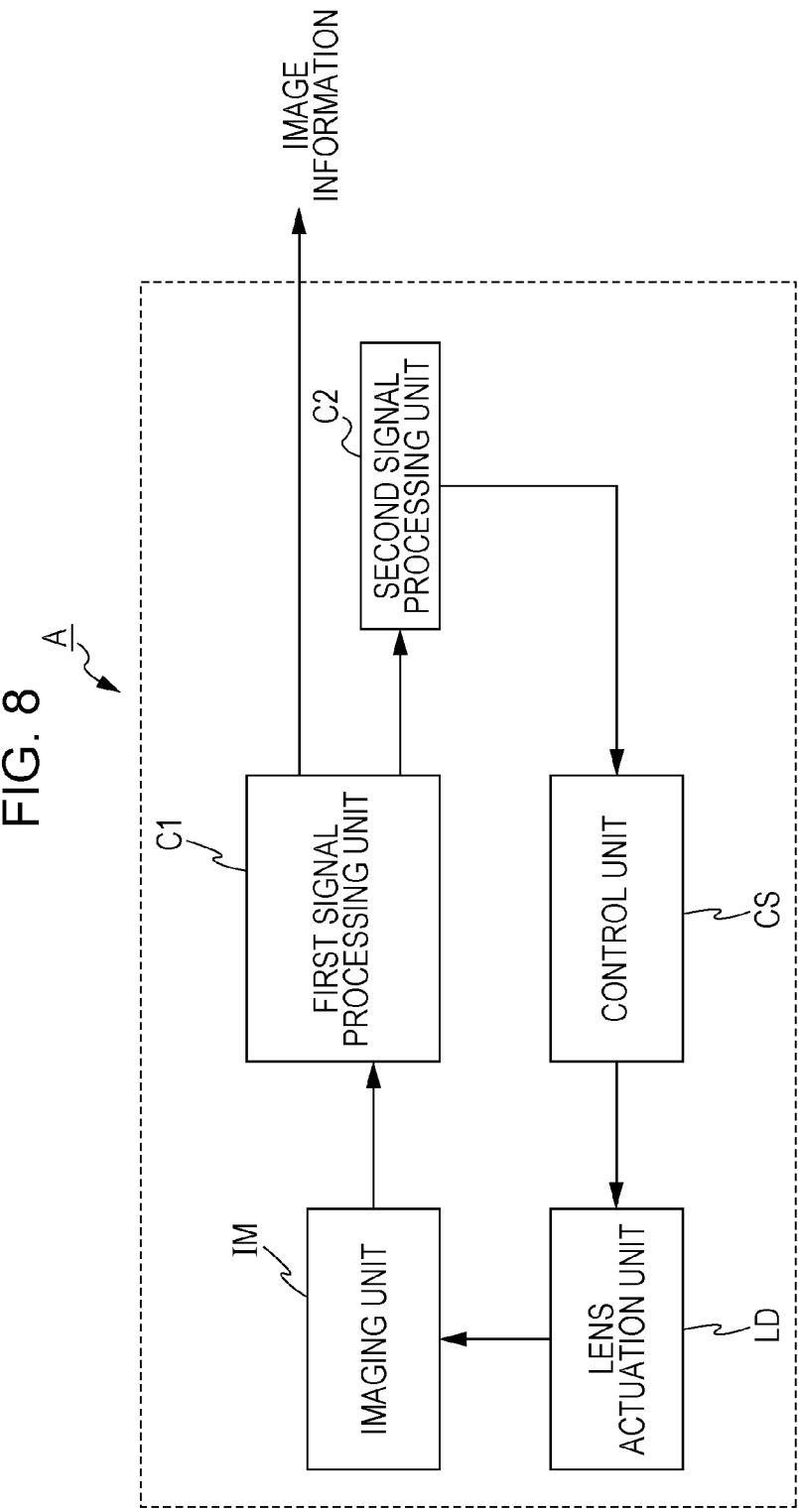

FIRST IMAGE INFORMATION (BASE IMAGE) ⟷ SECOND IMAGE INFORMATION (REFERENCE IMAGE)

GROUND LINE DIRECTION

IMAGING APPARATUS, IMAGING SYSTEM THAT INCLUDES IMAGING APPARATUS, ELECTRON MIRROR SYSTEM THAT INCLUDES IMAGING APPARATUS, AND RANGING APPARATUS THAT INCLUDES IMAGING APPARATUS

BACKGROUND

1. Technical Field

The present disclosure relates to an imaging apparatus, an imaging system that includes the imaging apparatus, an electron mirror system that includes the imaging apparatus, and a ranging apparatus that includes the imaging apparatuses.

2. Description of the Related Art

In the field of in-vehicle cameras, Japanese Unexamined Patent Application Publication No. 2010-25915, for example, discloses an imaging apparatus that includes polarizers disposed in an optical path of a compound-eye camera, and the polarizers are disposed such that the directions of their polarization axes differ from one another, in order to detect the road condition or lanes.

In addition, as cameras in the medical and cosmetic fields, such as an endoscope system and a skin analyzer system, imaging apparatuses that obtain both unpolarized light images and polarized light images are in practical use. Such an imaging apparatus includes a polarized illuminator that irradiates biological tissues with unpolarized light and light that vibrates in the direction of a predetermined polarization axis. When a biological tissue is irradiated with light of a predetermined polarization component, light reflected by the surface of the biological tissue results in specular reflection light in which the polarization component is retained, and light reflected by a deeper portion of the biological tissue results in diffuse reflection light having chaotic polarization components. Accordingly, images of the surface of the biological tissue and of the deeper portion of the biological tissue can be obtained by providing the imaging apparatus with a polarization filter that transmits light which vibrates in the direction parallel to the polarization axis of the polarized illuminator and another polarization filter that transmits light which vibrates in the direction orthogonal to the polarization axis of the polarized illuminator.

For example, Japanese Unexamined Patent Application Publication No. 2008-237243 and Japanese Unexamined Patent Application Publication No. 2011-97987 disclose imaging apparatuses for obtaining images having different polarization characteristics.

SUMMARY

With the conventional technique described above, however, there is a demand for an imaging apparatus that can capture a moving image with a simpler configuration.

One non-limiting and exemplary embodiment provides an imaging apparatus that can capture a moving image with a simpler configuration.

In one general aspect, the techniques disclosed here feature an imaging apparatus that includes a lens optical system, a color image sensor that includes at least a plurality of first pixels on which light that has passed through the lens optical system is incident and a plurality of second pixels on which light that has passed through the lens optical system is incident, and a first optical element array disposed between the lens optical system and the color image sensor. In the imaging apparatus, the lens optical system includes a plurality of optical regions, and the plurality of optical regions include a first optical region and a second optical region that differ in terms of at least one selected from the group of spectral transmittance characteristics and transmissive polarization characteristics. The plurality of first pixels include respective spectral filters having mutually different spectral transmittance characteristics, and the plurality of second pixels include respective spectral filters having at least one type of spectral transmittance characteristics. The first optical element array directs light that has passed through the first optical region to the plurality of first pixels and directs light that has passed through the second optical region to the plurality of second pixels. The first optical element array is a first lenticular lens, and the first lenticular lens is provided on the color image sensor.

According to the imaging apparatus of one embodiment of the present disclosure, a moving image can be captured with a simple configuration.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is a block diagram illustrating an imaging apparatus according to a third embodiment of the present disclosure;

DETAILED DESCRIPTION

Figure 1:
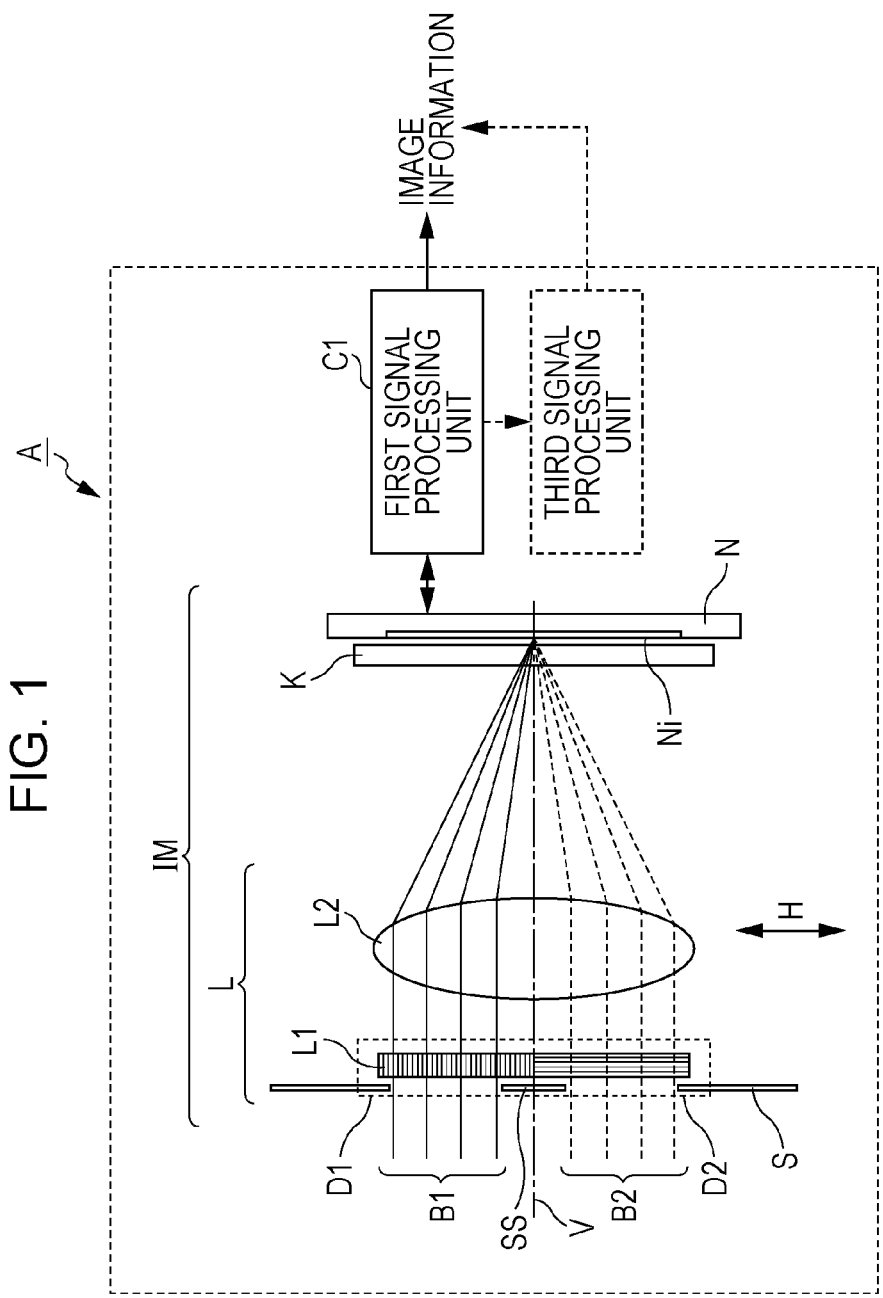
FIG. 1 is a schematic diagram illustrating an imaging apparatus according to a first embodiment of the present disclosure.

An imaging apparatus and an imaging system according to an embodiment of the present disclosure are as follows.

An imaging apparatus according to one embodiment of the present disclosure includes a lens optical system, a color image sensor that includes at least a plurality of first pixels on which light that has passed through the lens optical system is incident and a plurality of second pixels on which light that has passed through the lens optical system is incident, and a first optical element array disposed between the lens optical system and the color image sensor. In the imaging apparatus, the lens optical system includes a plurality of optical regions, and the plurality of optical regions include a first optical region and a second optical region that differ in terms of at least one selected from the group of spectral transmittance characteristics and transmissive polarization characteristics. The plurality of first pixels include respective spectral filters having mutually different spectral transmittance characteristics, and the plurality of second pixels include respective spectral filters having at least one type of spectral transmittance characteristics. The first optical element array directs light that has passed through the first optical region to the plurality of first pixels and directs light that has passed through the second optical region to the plurality of second pixels. The first optical element array is a first lenticular lens, and the first lenticular lens is provided on the color image sensor.

According to the imaging apparatus of one aspect of the present disclosure, a plurality of images that differ in polarization characteristics or a plurality of images that differ in spectral characteristics can be obtained simultaneously by using a single imaging system.

The color image sensor may further include a plurality of third pixels on which light that has passed through the lens optical system is incident, and a plurality of fourth pixels on which light that has passed through the lens optical system is incident. The plurality of optical regions in the lens optical system may further include a third optical region and a fourth optical region. The first optical region, the second optical region, the third optical region, and the fourth optical region may differ in terms of at least one selected from the group of spectral transmittance characteristics and transmissive polarization characteristics. The plurality of third pixels and the plurality of fourth pixels may include respective spectral filters having mutually different spectral transmittance characteristics. The first optical element array may direct light that has passed through the third optical region to the plurality of third pixels and direct light that has passed through the fourth optical region to the plurality of fourth pixels.

The first optical region may be constituted by a polarization filter that primarily transmits light which vibrates in a direction of a first polarization axis, and the second optical region may be constituted by another polarization filter that primarily transmits light which vibrates in a direction of a second polarization axis that is different from the first polarization axis.

The first optical region may transmit unpolarized light, and the second optical region may be constituted by a polarization filter that primarily transmits light which vibrates in a direction of a predetermined polarization axis.

The first optical region may be constituted by a spectral filter that primarily transmits light in a visible-light spectrum, and the second optical region may be constituted by another spectral filter that primarily transmits light in a non-visible-light spectrum.

The imaging apparatus may further include a second lenticular lens disposed between the first lenticular lens and the color image sensor, and the first lenticular lens may be provided on the color image sensor with the second lenticular lens provided therebetween.

The second lenticular lens may be a binary distributed refractive-index element or a multi-level distributed refractive-index element.

The imaging apparatus may further include a microlens disposed between the first lenticular lens and the color image sensor, and the first lenticular lens may be provided on the color image sensor with the microlens provided therebetween.

The microlens may be a binary distributed refractive-index element or a multi-level distributed refractive-index element.

The imaging apparatus may further include a first signal processor that, in operation, generates first image information and second image information on the basis of pixel signals obtained from the plurality of first pixels and the plurality of second pixels, respectively.

The imaging apparatus may further include a second signal processor that, in operation, generates parallax information of an object on the basis of the first image information and the second image information, a controller that, in operation, generates a focus control signal on the basis of the parallax information, and a lens actuator. The lens optical system may include at least one lens movable along an optical axis of the lens optical system, and the lens actuator may move the lens along the optical axis on the basis of the focus control signal.

The imaging apparatus may further include a third signal processor. The third signal processor, in operation, may read brightness of at least one selected from the group of the first image information and the second image information, compare the brightness with a predetermined threshold value, and output at least one selected from the group of the first image information and the second image information in accordance with a result of the comparison.

The imaging apparatus may further include a third signal processor. The third signal processor, in operation, may read brightness of at least one selected from the group of the first image information and the second image information, determine an addition ratio of the first image information and the second image information in accordance with the brightness, generate an added image obtained by adding the first image information and the second image information in accordance with the addition ratio, and output the added image.

An imaging system according to one embodiment of the present disclosure includes any one of the imaging apparatuses described above, and a polarized illuminator that emits polarized light.

The imaging system may further include a display that, in operation, displays an image obtained by the imaging apparatus.

An electron mirror system according to one embodiment of the present disclosure includes any one of the imaging apparatuses described above, and a display that, in operation, displays an image obtained by the imaging apparatus.

The electron mirror system may further include a polarized illuminator that emits polarized light. The imaging apparatus, the polarized illuminator, and the display may be disposed along substantially the same plane.

The electron mirror system may further include a third signal processor that, in operation, generates information in which a feature of an object is quantified by using the first image information and the second image information, and the display, in operation, may further display the quantified information. The electron mirror system may further include a second signal processor that, in operation, generates parallax information of the object on the basis of the first image information and the second image information and generates information for moving a position of the object. The display, in operation, may further display information for changing a distance between the object and the display.

An imaging system according to one embodiment of the present disclosure includes any one of the imaging apparatuses described above, and one of a near-infrared illuminator and a near-ultraviolet illuminator.

A ranging apparatus according to one embodiment of the present disclosure includes any one of the imaging apparatuses in a plurality.

First Embodiment

FIG. 1 is a schematic diagram illustrating an imaging apparatus A according to a first embodiment. The imaging apparatus A according to the present embodiment includes an imaging unit IM and a first signal processing unit C1. The imaging unit IM that includes a lens optical system L having an optical axis V, a lenticular lens K disposed in the vicinity of a focal point of the lens optical system L, and a color image sensor N.

The lens optical system L includes a stop S through which light from an object (not illustrated) passes, an optical element L1 on which light that has passed through the stop S is incident, and a lens L2 on which light that has passed through the optical element L1 is incident. The lens optical system L includes first and second optical regions D1 and D2.

The lens L2 may be constituted by a single lens or a plurality of lenses. The lens L2 may be constituted by a plurality of lenses that are disposed so as to sandwich the stop S. FIG. 1 illustrates the lens L2 that is constituted by a single lens.

The optical element L1 is disposed in the vicinity of the stop S. The optical element L1 includes a portion corresponding to the first optical region D1, and another portion corresponding to the second optical region D2. A polarization filter that transmits light which vibrates in the direction of a first polarization axis, a transmission axis, is provided in the first optical region D1. Another polarization filter that transmits light which vibrates in the direction of a second polarization axis, a transmission axis orthogonal to the first polarization axis, is provided in the second optical region D2.

Edges of the respective polarization filters are present at an interface between the first optical region D1 and the second optical region D2, and thus a light-blocking region SS is provided so as to prevent light from being incident on the edges of the polarization filters.

In the present embodiment, light that has passed through either of the optical regions D1 and D2 passes through the lens L2, and is then incident on the lenticular lens K. The lenticular lens K directs light that has passed through the optical region D1 to a plurality of pixels P1 provided in the color image sensor N, and directs light that has passed through the optical region D2 to a plurality of pixels P2 provided in the color image sensor N. The color image sensor N subjects the light incident on the pixels P1 and P2 to photoelectric conversion, and converts the light to pixel signals in accordance with the intensity of the incident light. A pixel signal is a signal that indicates luminance information generated through photoelectric conversion in the pixels P1 or P2. The first signal processing unit C1 receives pixel signals from the color image sensor N. Then, the first signal processing unit C1 generates, from luminance information of a pixel group that includes the plurality of pixels P1, image information of an image formed by light that vibrates in the direction of the first polarization axis, and outputs the generated image information. In addition, the first signal processing unit C1 generates, from luminance information of a pixel group that includes the plurality of pixels P2, image information of an image formed by light that vibrates in the direction of the second polarization axis, and outputs the generated image information. The first signal processing unit C1 may be constituted by an electronic circuit and so on, or may be constituted by a calculation device, a memory, and software.

In FIG. 1, a light beam B1 indicates a light beam that passes through the first optical region D1 of the optical element L1, whereas a light beam B2 indicates a light beam that passes through the second optical region D2 of the optical element L1. The light beams B1 and B2 pass through the stop S, the optical element L1, the lens L2, and the lenticular lens K in this order, and reach an imaging surface Ni of the color image sensor N.

Figure 2:
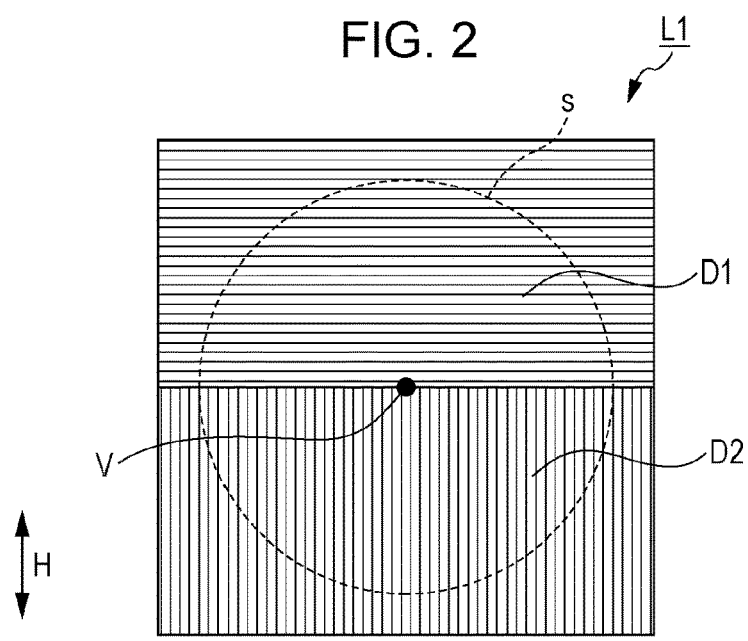
FIG. 2 is a front view, as viewed from an object, of first and second optical regions in an optical element according to the first embodiment of the present disclosure.

FIG. 2 is a front view, as viewed from the object, of the first optical region D1 and the second optical region D2. The first optical region D1 and the second optical region D2 of the optical element L1 are located in respective spaces that are divided by a plane containing the optical axis V. In FIG. 2, a broken line s indicates an aperture region in the stop S. In addition, an arrow H illustrated in FIGS. 1 and 2 indicates a horizontal direction when the imaging apparatus A is in use.

Figure 3:
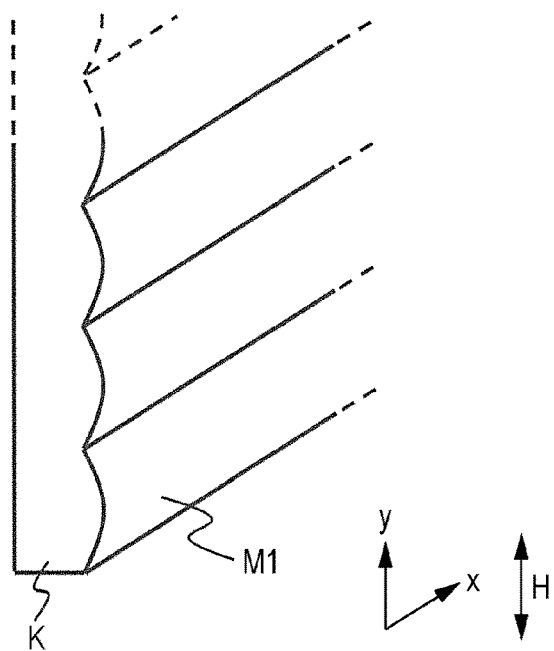
FIG. 3 is a perspective view of a lenticular lens according to the first embodiment of the present disclosure.

FIG. 3 is a perspective view of the lenticular lens K. The lenticular lens K includes a plurality of cylindrical lenses M1. Each cylindrical lens M1 extends in an x-direction (first direction), and the plurality of cylindrical lenses M1 are arrayed in a y-direction (second direction). The y-direction corresponds to the horizontal direction indicated in FIGS. 1 and 2. A section of each cylindrical lens M1 along a plane orthogonal to the x-direction has a curve that protrudes toward the color image sensor N. In the present embodiment, the x-direction and the y-direction are orthogonal to each other.

As illustrated in FIG. 1, the lenticular lens K is disposed in the vicinity of the focal point of the lens optical system L and is spaced apart from the imaging surface Ni by a predetermined distance.

Figure 4A:
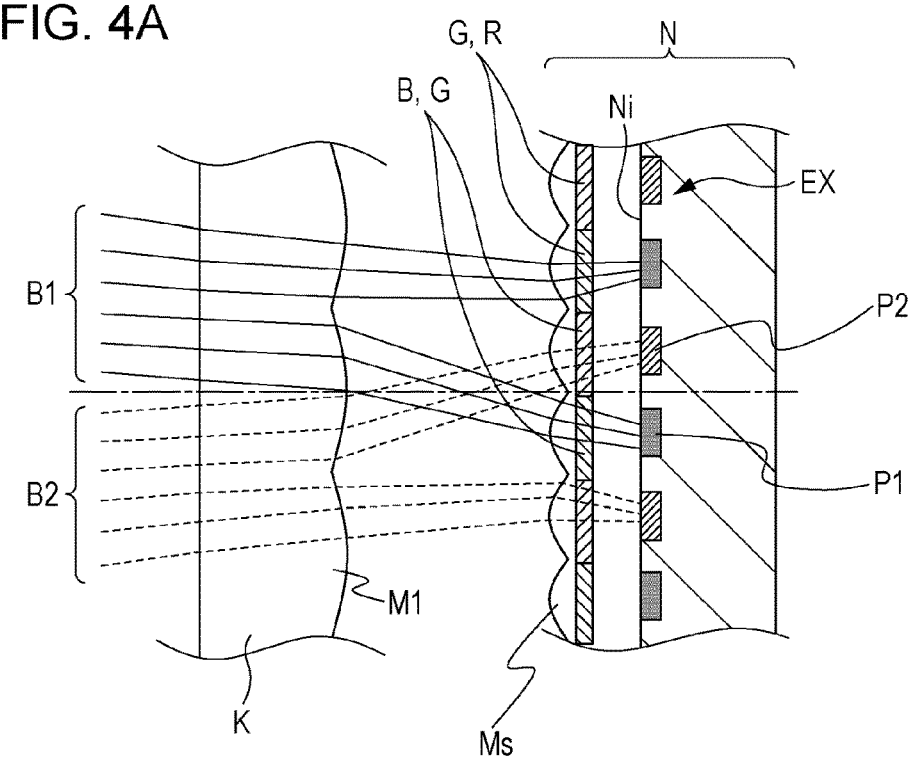
FIG. 4A is an enlarged view of the lenticular lens and a color image sensor illustrated in FIG. 1 according to the first embodiment.
Figure 4B:
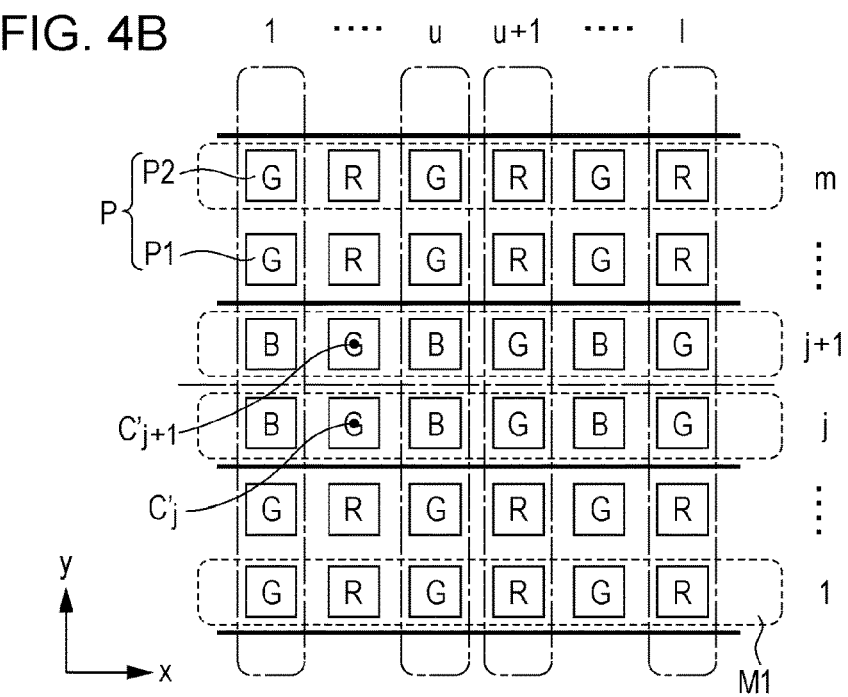
FIG. 4B illustrates a positional relationship between the lenticular lens and pixels in the color image sensor.

FIG. 4A is an enlarged view of the lenticular lens K and the color image sensor N illustrated in FIG. 1; and FIG. 4B illustrates a positional relationship between the lenticular lens K and pixels in the color image sensor N. The lenticular lens K is disposed such that a face where the cylindrical lenses M1 are provided faces the imaging surface Ni.

The color image sensor N includes the imaging surface Ni and a plurality of pixels P. As illustrated in FIG. 4B, the plurality of pixels P are arrayed two-dimensionally in the x-direction and the y-direction. An array extending in the x-direction is referred to as a row, whereas an array extending in the y-direction is referred to as a column. In that case, the plurality of pixels P are arrayed, for example, in m rows by I columns (m and I are each an integer equal to or greater than 2) in the imaging surface Ni. In other words, m rows of pixel groups, in each of which I pixels are arrayed from 1 in the x-direction, are arrayed from the first row to the mth row in the y-direction.

Among the m rows of the pixel groups, a midpoint $C'_j$ in I pixels arrayed in a jth row ($1 \leq j < m$) in the x-direction is substantially aligned in the y-direction with a midpoint $C'_{j+1}$ in I pixels arrayed in a (j+1)th row in the x-direction.

In a similar manner, it is possible to consider that the plurality of pixels P are arrayed such that I columns of pixel groups, in each of which a plurality of pixels are arrayed in the y-direction, are arrayed from the first to the Ith column in the x-direction. In this case, among the I columns of the pixel groups, a midpoint in m pixels arrayed in a uth column ($1 \leq u < I$) in the y-direction is substantially aligned in the x-direction with a midpoint in m pixels arrayed in a (u+1)th column in the y-direction.

The plurality of pixels P are divided into the plurality of pixels P1 and the plurality of pixels P2 that are each arrayed in the x-direction and that constitute respective rows. The plurality of pixels P1 and the plurality of pixels P2 are arrayed in the respective rows in the x-direction, as described above. In the y-direction, rows constituted by the pixels P1 and rows constituted by the pixels P2 are disposed in an alternating manner. The lenticular lens K is disposed in such a manner that each of the plurality of cylindrical lenses M1 constituting the lenticular lens K corresponds to two rows of pixel groups: a row of a pixel group constituted by the pixels P1 provided in the imaging surface Ni and another row of a pixel group constituted by the pixels P2 provided in the imaging surface Ni. Microlenses Ms are provided on the imaging surface Ni so as to cover the surfaces of the pixels P1 and P2.

In the present embodiment, the plurality of pixels P1 and the plurality of pixels P2 have an identical shape in the imaging surface Ni. For example, the plurality of first pixels P1 and the plurality of second pixels P2 have an identical rectangular shape and have areas that are equal to one another.

In addition, the pixels P1 and P2 are disposed underneath the respective microlenses Ms, and each include a photoelectric conversion unit EX, which is provided in the imaging surface Ni, and one of a color filter R (red), a color filter G (green), and a color filter B (blue), which are provided on the respective photoelectric conversion units EX. In the pixels P1 and P2, the color filters R (red), the color filters G (green), and the color filters B (blue) are arrayed in a manner as illustrated in FIG. 4B. Specifically, pixels provided with the color filters G (green) and pixels provided with the color filters R (red) are arrayed in an alternating manner in the x-direction in a unit region, on the imaging surface Ni, corresponding to one of the cylindrical lenses M1 of the lenticular lens K. In another unit region that is adjacent to the aforementioned unit region in the y-direction, pixels provided with the color filters B (blue) and pixels provided with the color filters G (green) are arrayed in an alternating manner in the x-direction.

Thus, when one looks at only the rows of the pixel groups constituted by the pixels P1, rows of pixel groups constituted by the pixels provided with the color filters B (blue) and the pixels provided with the color filters G (green) and rows of pixel groups constituted by the pixels provided with the color filters G (green) and the pixels provided with the color filters R (red) are arrayed in an alternating manner. In a similar manner, when one looks at only the rows of the pixel groups constituted by the pixels P2, rows of pixel groups constituted by the pixels provided with the color filters B (blue) and the pixels provided with the color filters G (green) and rows of pixel groups constituted by the pixels provided with the color filters G (green) and the pixels provided with the color filters R (red) are arrayed in an alternating manner. Accordingly, even if an image is formed only by the rows of the pixel groups constituted by the pixels P1 or only by the rows of the pixel groups constituted by the pixels P2, a resulting image includes pixel signals corresponding to luminance values obtained from the pixels provided with the color filters R, G, B. Thus, a color image is obtained in either case.

The lenticular lens K is designed such that most of a light beam (the light beam B1 indicated by solid lines in FIG. 1) that passes through the optical region D1 (illustrated in FIGS. 1 and 2) of the optical element L1 reaches the pixels P1 provided in the imaging surface Ni and most of a light beam (the light beam B2 indicated by broken lines in FIG. 1) that passes through the optical region D2 reaches the pixels P2 provided in the imaging surface Ni. Specifically, the stated configuration is achieved by setting parameters, such as the refractive index of the lenticular lens K, the distance from the imaging surface Ni, and the radius of curvature of the surface of each cylindrical lens M1, as appropriate.

The stop S is a region through which light beams at the entire angles of view pass. Therefore, by providing a plane having optical characteristics that control polarization characteristics in the vicinity of the stop S, the polarization characteristics of the light beams at the entire angles of view can be controlled in a similar manner. In other words, in the present embodiment, the optical element L1 may be provided in the vicinity of the stop S. Providing the first and second optical regions D1 and D2 of the optical element L1 in the vicinity of the stop S makes it possible to provide light beams with polarization characteristics corresponding to the number of divided regions.

Referring to FIG. 1, the stop S is provided at such a position that light that has passed through the stop S is directly incident on the optical element L1 without involving other optical members. The optical element L1 may be provided on a side of the stop S that is closer to the object. In this case, light that has passed through the optical element L1 may directly pass through the stop S without involving other optical members.

In addition, the lenticular lens K has a function of emitting light in an assigned direction in accordance with the angle of incidence of a light ray. Therefore, light beams can be directed to assigned pixels in the imaging surface Ni so as to correspond to the first and second optical regions D1 and D2, which are divided in the vicinity of the stop S.

Through the configuration described above, first color image information having information on polarized light that vibrates in the direction of the first polarization axis and second color image information having information on polarized light that vibrates in the direction of the second polarization axis, which is orthogonal to the first polarization axis, can be obtained simultaneously by using luminance information of the pixel groups constituted by the pixels P1 and luminance information of the pixel groups constituted by the pixels P2. In other words, through the configuration described above, image information at a total of six channels can be obtained simultaneously through combinations of the optical regions D1 and D2 and the R, G, and B pixels. In addition, as the first polarization axis and the second polarization axis are orthogonal to each other, by adding and averaging the first color image information and the second color image information, third color image information of unpolarized light can also be generated.

According to the above-described configuration, a given pixel P1 is disposed so as to be adjacent to another pixel P1 in the x-direction, and the pixels P1 and the pixels P2 are disposed in an alternating manner in the y-direction. In a similar manner, as for the pixels P2, a given pixel P2 is disposed so as to be adjacent to another pixel P2 in the x-direction, and the pixels P2 and the pixels P1 are disposed in an alternating manner in the y-direction. Thus, as compared with a case in which a single image is obtained from the entire pixels in the color image sensor N, the resolution of each of the first color image information and the second color image information is the same as the resolution of the image in the aforementioned case in the x-direction, and is one-half the resolution of the image in the aforementioned case in the y-direction. In other words, the number of effective pixels is reduced by one-half. Therefore, two images formed by light beams with different polarization directions can be obtained simultaneously with a decrease in the resolution by one-half as compared with a case in which a single image is obtained from the entire pixels in the color image sensor N. In the meantime, in a case in which an optical element L1 is divided into four optical regions and each microlens is disposed so as to correspond to 2×2 pixels so that light beams that have passed through the four optical regions are directed to respective pixels by the microlenses, the numbers of effective pixels in the x-direction and in the y-direction are each reduced to one-half, and the number of effective pixels and the resolution as a whole are reduced to one-fourth. Accordingly, the present embodiment makes it possible to obtain an image having a resolution that is twice the resolution of an image to be obtained in a case in which the optical element L1 is divided into four optical regions. It is to be noted that the decrease in the number of effective pixels and the decrease in the resolution occur as light beams that have passed through respective divided optical regions are directed to the respective pixels, and are not caused by the color filters being disposed. In a conventional imaging apparatus, when color filters are arrayed in a Bayer array, combinations of color filters are repeated per 2×2 pixels, but the resolution can be retained through interpolation processing. For example, in the case of the Bayer array, when the number of pixels in an image in the vertical direction is 1000, the resolution of approximately 1000 TV lines can be obtained through the interpolation processing if the lens performance is sufficient.

In addition, according to the present embodiment, light is divided into its spectral components through the color filters provided on the pixels in the image sensor, and thus a naturally-blurred color image can be obtained even outside the depth of field. On the other hand, if color filters are provided in optical regions of the optical element L1, parallactic color misregistration occurs in an object outside the depth of field, and thus an unnaturally-blurred color image may be obtained. In addition, if a color filter to be provided in an optical region of the optical element L1 is constituted by a dielectric multilayer film, multipath reflection may occur between the dielectric multilayer film and the imaging surface Ni of the color image sensor N and so on, and a ghost image may appear. In addition, the spectral transmittance characteristics of a dielectric multilayer film vary in accordance with the angle of incidence, and thus color shading may occur if a color filter is provided in an optical region of the optical element L1.

Furthermore, according to the present embodiment, light beams that pass through the respective optical regions D1 and D2 of the optical element L1 are directed to the respective pixels P1 and P2 by the lenticular lens K. Thus, even if crosstalk occurs by the lenticular lens K, the crosstalk occurs only in one direction. Accordingly, less crosstalk occurs and the separability of image signals is high as compared with a case in which the optical element L1 is divided into four optical regions and light beams are directed to respective four pixels by a microlens.

In addition, since the optical element L1 is divided into two optical regions, the area of the light-blocking region to be located at the boundary of the optical regions can be kept small, as compared with the case in which the optical element L1 is divided into four optical regions. Thus, a decrease in the sensitivity due to the light-blocking region can be suppressed.

Although the optical region D1 and the optical region D2 of the optical element L1 are constituted by polarization filters having different polarization axes in the present embodiment, a configuration may be such that a transparent glass plate is provided in the optical region D1 and a polarization filter that transmits light which vibrates in the direction of the first polarization axis is provided in the optical region D2. Alternatively, a configuration may be such that no element is provided in the optical region D1 and a polarization filter that transmits light which vibrates in the direction of the first polarization axis is provided in the optical region D2.

Through such a configuration, first color image information having information on unpolarized light and second color image information having information on polarized light that vibrates in the direction of the first polarization axis can be obtained simultaneously by using luminance information of the pixel groups constituted by the pixels P1 and luminance information of the pixel groups constituted by the pixels P2. In addition, third color image information having information on polarized light that vibrates in the direction of the second polarization axis, which is orthogonal to the first polarization axis, can also be generated by multiplying the first color image information by a coefficient that is 2×the transmittance of the polarization filter and then subtracting the second color image information from the product.

As another alternative, a configuration may be such that filters having different spectral transmittance characteristics are provided in the optical region D1 and the optical region D2 of the optical element L1. For example, the optical region D1 is constituted by a spectral filter that primarily transmits visible light, and the optical region D2 is constituted by another spectral filter that primarily transmits near-infrared light or near-ultraviolet light.

Through such a configuration, primarily visible light is incident on the pixels P1, and thus color image information having information on the visible light can be obtained by using luminance information of the pixel groups constituted by the pixels P1. Meanwhile, primarily near-infrared light or near-ultraviolet light is incident on the pixels P2, and the color filters R (red), G (green), and B (blue) provided on the image sensor transmit the near-infrared light and the near-ultraviolet light. Thus, image information having information on the near-infrared light or the near-ultraviolet light can be obtained by using luminance information of the pixel groups constituted by the pixels P2. In this manner, the color image information having information on the visible light and the image information having information on the near-infrared light or the near-ultraviolet light can be obtained simultaneously.

Figure 5A:
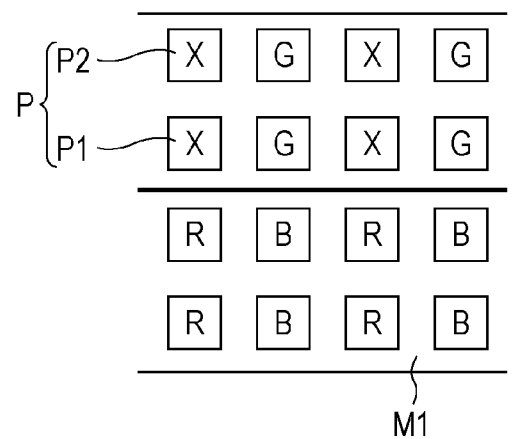
FIG. 5A illustrates a positional relationship between a lenticular lens and pixels in a color image sensor according to a modification of the first embodiment.
Figure 5B:
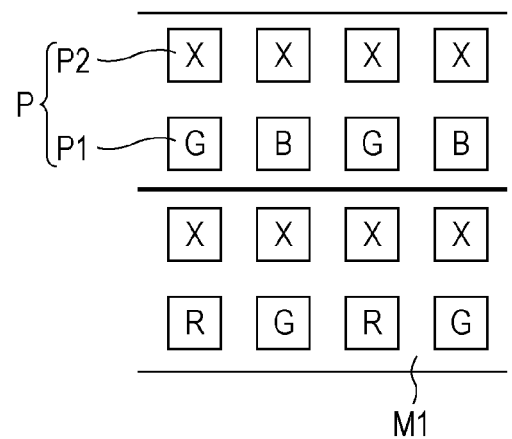
FIG. 5B illustrates a positional relationship between a lenticular lens and pixels in a color image sensor according to another modification of the first embodiment.

In addition, although the color filters R (red), G (green), and B (blue) are provided on the image sensor in the present embodiment, a different configuration of color filters may be employed. For example, as illustrated in FIGS. 5A and 5B, color filters R (red), G (green), B (blue), and X (color in any given spectrum) may be provided on the image sensor. The color in any given spectrum, for example, is a color in a spectrum of white (entire visible light spectrum), a spectrum of a complementary color, such as cyan, or a spectrum of non-visible light, such as near-infrared light or near-ultraviolet light, in the case of the configuration illustrated in FIG. 5A. Through such a configuration, additional piece of spectral information can be used when images based on the two polarization axes are obtained simultaneously or when image information based on polarized light and image information based on unpolarized light are obtained simultaneously. Alternatively, in the case of the configuration illustrated in FIG. 5B, the color X in any given spectrum may be set to a color in any one of the spectra of R (red), G (green), and B (blue), or may be set to a color in a spectrum of white (visible light), a spectrum of a complementary color, such as cyan, or a spectrum of non-visible light, such as near-infrared light or near-ultraviolet light. Through such a configuration, the pixels P2 are reserved for image information only in a predetermined spectrum, and thus the resolution of image information corresponding to the information of the optical region D2 can be increased. For example, a transparent glass plate is provided in the optical region D1; a polarization filter that transmits light which vibrates in the direction of the first polarization axis is provided in the optical region D2; color filters are arrayed as illustrated in FIG. 5B; and the color filter X of cyan is used. In this case, a color image can be generated by using luminance information of the pixel groups constituted by the pixels P1, and a high-resolution polarized light image of a single color of cyan can be generated by using luminance information of the pixel groups constituted by the pixels P2. Alternatively, a spectral filter that primarily transmits visible light is provided in the optical region D1; another spectral filter that primarily transmits near-infrared light or near-ultraviolet light is provided in the optical region D2; color filters are arrayed as illustrated in FIG. 5B; and the color filter X of white is used. In this case, a color image can be generated by using luminance information of the pixel groups constituted by the pixels P1, and high-resolution, highly-sensitive image information having information on the near-infrared light or the near-ultraviolet light can be generated by using luminance information of the pixel groups constituted by the pixels P2. The spectral filter to be provided in the optical region D2 may be an absorbing spectral filter. In addition, the above-described configuration may partially constitute an imaging system that includes a near-infrared light or near-ultraviolet light illuminator.

Second Embodiment

A second embodiment differs from the first embodiment in that a lenticular lens is provided on the imaging surface of the color image sensor N. Here, detailed descriptions of content in the present embodiment that is similar to the content in the first embodiment will be omitted.

Figure 6A:
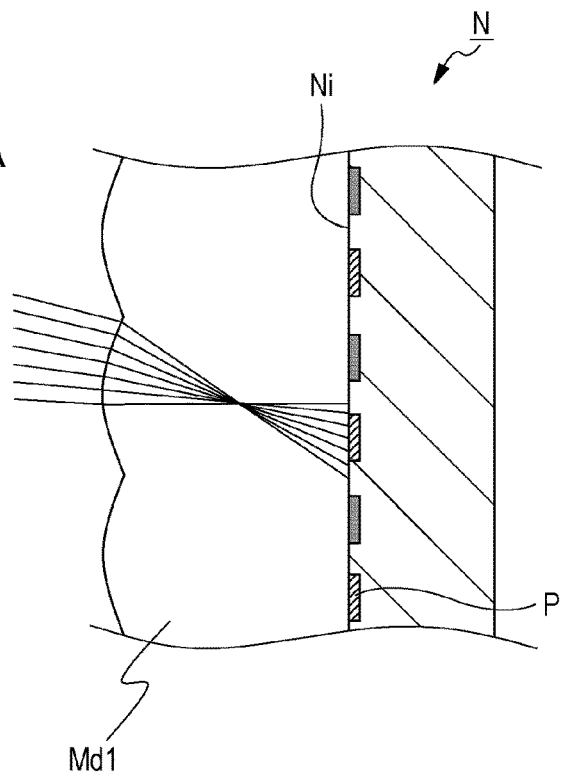
FIG. 6A is an enlarged view of a lenticular lens and a color image sensor according to a second embodiment of the present disclosure.
Figure 6B:
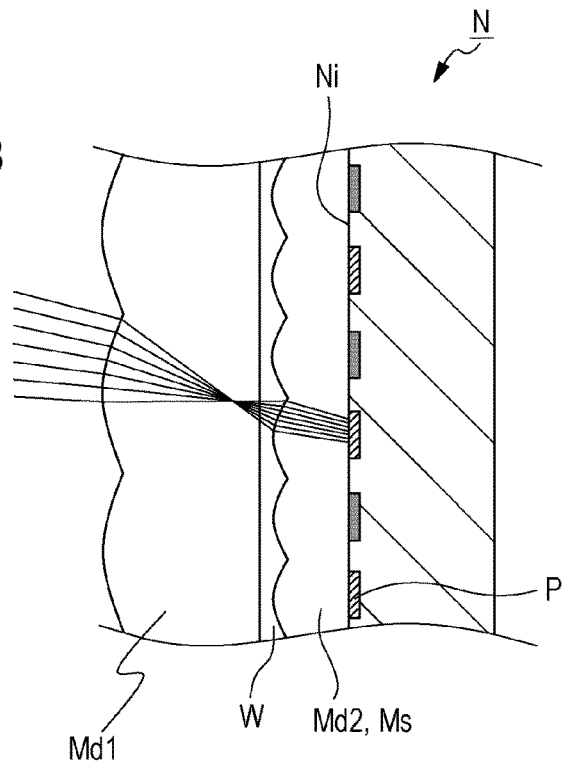
FIG. 6B is an enlarged view of a lenticular lens and a color image sensor according to a modification of the second embodiment of the present disclosure.

FIGS. 6A and 6B are enlarged views of the lenticular lens and the color image sensor N, in which only light rays that have passed through one of the optical regions are illustrated. In the present embodiment, a lenticular lens Md1 is provided on the imaging surface Ni of the color image sensor N. As in the first embodiment, the pixels P are disposed in a matrix in the imaging surface Ni. Each cylindrical lens of a plurality of cylindrical lenses constituting the lenticular lens Md1 corresponds, among the plurality of pixels P, to two rows of pixels P: a row of a pixel group constituted by the pixels P1 and another row of a pixel group constituted by the pixels P2. As in the first embodiment, in the present embodiment as well, light beams that have passed through different optical regions can be guided to the respective pixels. FIG. 6B illustrates a modification of the present embodiment. In the configuration illustrated in FIG. 6B, a lenticular lens Md2 (or microlenses Ms) is provided so as to cover the pixels P, and the lenticular lens Md1 is disposed on the lenticular lens Md2 (or microlenses Ms) with a low-refractive-index layer W provided therebetween. Through the configuration illustrated in FIG. 6B, convergence efficiency can be enhanced as compared with the configuration illustrated in FIG. 6A. In a case in which the lenticular lens Md2 is used, each cylindrical lens of a plurality of cylindrical lenses constituting the lenticular lens Md2 corresponds to a row of a pixel group constituted by the pixels P1 or to a row of a pixel group constituted by the pixels P2. Alternatively, in a case in which the microlenses Ms are used, each microlens Ms corresponds to a single pixel P1 or to a single pixel P2.

When the lenticular lens K is being separated from the color image sensor N as in the first embodiment, it is difficult to position the lenticular lens K and the color image sensor N relative to each other. However, when the lenticular lens Md1 is provided on the color image sensor N as in the present embodiment, the lenticular lens Md1 and the color image sensor N can be positioned relative to each other through a wafer process, and thus the positioning can be achieved with ease and with high precision.

Figure 7A:
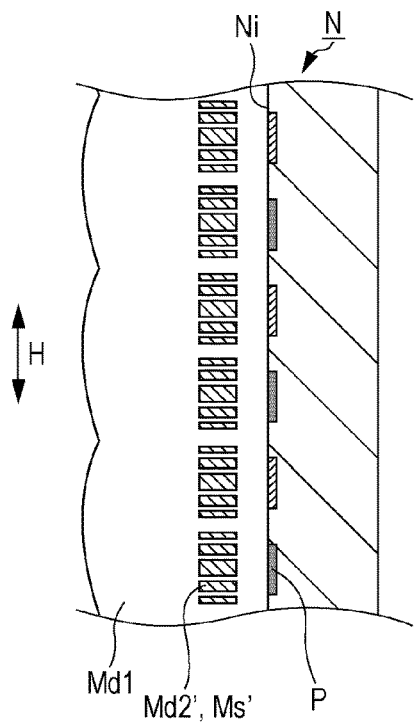
FIG. 7A is a sectional view of a diffractive optical element that can be provided on an image sensor according to a modification of the second embodiment of the present disclosure.
Figure 7B:
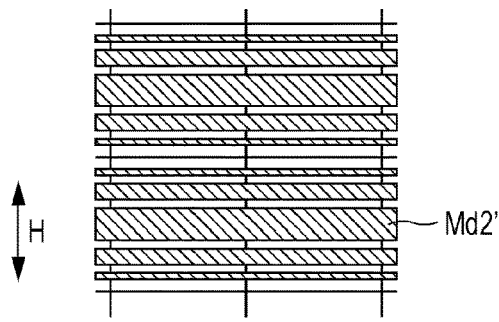
FIG. 7B is another sectional view thereof.
Figure 7C:
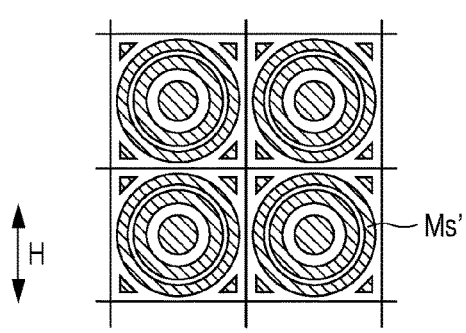
FIG. 7C is another sectional view thereof.

In addition, in the second embodiment, aside from the lenticular lens provided over the pixels in the image sensor, the microlenses Ms having a different shape may further be provided on the image sensor. For example, as disclosed in Japanese Unexamined Patent Application Publication No. 2008-10773, a distributed refractive-index element that causes light to converge through a distribution of materials having different refractive indices may be used. FIG. 7A is a sectional view illustrating an example of a diffractive optical element Md2' (Ms'); FIG. 7B is another sectional view of the diffractive optical element Md2'; and FIG. 7C is a sectional view of the diffractive optical element Ms'. Referring to FIGS. 7A, 7B, and 7C, optical member portions indicated by hatching are formed of a material or a medium having a refractive index different from that of a material or a medium by which portions surrounding the optical member portions are formed. As illustrated in FIG. 7B, the diffractive optical element Md2' has a stripe pattern on a planar face thereof that is parallel to a planar face in which the pixels are provided, and the stripe pattern is formed such that the width of the stripe decreases as the distance from the center of the pixel increases. The refractive index of the diffractive optical element Md2' may be adjusted by adjusting the difference between the refractive index of the optical members and the refractive index of the portions surrounding the optical members, by adjusting the widths of the stripes, or by adjusting the intervals of the stripes. The arrangement of the optical members is not limited to the one having line symmetry in the H-direction relative to the center of the pixel, and may not have line symmetry in the H-direction relative to the center of the pixel. In addition, as illustrated in FIG. 7C, the diffractive optical element Ms', for example, has a ring pattern along a planar face that is parallel to a planar face in which the pixels are provided, and is constituted by a plurality of cylindrical optical members that extend in a direction orthogonal to the planar face and that are disposed concentric with one another. The refractive index of the diffractive optical element Ms' may be adjusted by adjusting the difference between the refractive index of the optical members and the refractive index of the portions surrounding the optical members, by adjusting the sizes of the cylinders, or by adjusting the intervals of the cylinders disposed so as to be concentric with one another. The shape of the optical member is not limited to be cylindrical, and may be rotationally asymmetric about the optical axis. In addition, although FIGS. 7A, 7B, and 7C illustrate examples in which the diffractive optical element is a two-level binary diffractive optical element, the diffractive optical element may be a multi-level diffractive optical element of three or more levels.

The diffractive optical element Md2' and the diffractive optical element Ms' having the above-described structures can be fabricated, for example, through a semiconductor photolithography technique. A microlens having a conventional lens surface is fabricated, for example, by thermally deforming a resin, and it is thus difficult to provide a plurality of microlenses having mutually different curvatures of lens surfaces on a plurality of pixels in an image sensor. On the other hand, when the diffractive optical element Md2' or the diffractive optical element Ms' is used, the optical characteristics can be varied among the plurality of pixels in the image sensor by varying the aforementioned sizes of the optical members. Accordingly, even in a case in which light rays are incident obliquely on the pixels in the color image sensor N via the lens optical system L and the lenticular lens K, the light can converge on the pixels with high efficiency.

Third Embodiment

A third embodiment differs from the first and second embodiments in that a second signal processing unit, a lens actuation unit, and a control unit are further provided. The second signal processing unit generates parallax information of an imaging object from first image information and second image information generated by the first signal processing unit. The control unit controls the focus on the basis of the parallax information. Here, detailed descriptions of content in the present embodiment that is similar to the content in the first and second embodiments will be omitted.

FIG. 8 is a block diagram illustrating an imaging apparatus A according to the third embodiment. The imaging apparatus A includes the imaging unit IM, the first signal processing unit C1, a second signal processing unit C2, a control unit CS that controls the focus, and a lens actuation unit LD. The second signal processing unit C2 and the control unit CS that controls the focus may each be constituted by an electronic circuit and so on, or may be constituted by a calculation device, a memory, and software. In addition, the lens actuation unit LD includes an actuator that moves the lens L2 in the direction of the optical axis V. In the lens optical system L, the lens L2 is configured to be movable in the direction of the optical axis V.

First, the first signal processing unit C1 generates first image information and second image information by using, respectively, luminance information of a pixel group constituted by the pixels P1 and luminance information of a pixel group constituted by the pixels P2, which are obtained from the imaging unit IM. The first image information and the second image information are generated on the basis of respective light beams that have passed through different optical regions in the vicinity of the stop, and thus include parallax corresponding to the distances from the object.

Subsequently, the second signal processing unit C2 calculates the parallax by using the first image information and the second image information. Here, the first image information and the second image information include different polarization information or different spectral information, and thus the first image information and the second image information differ in luminance. Therefore, the first image information and the second image information are subjected to preprocessing that is necessary for extracting parallax information, for example, by normalizing the luminance or extracting edges prior to calculating the parallax. The parallax is extracted through pattern matching of image misregistration generated between a predetermined image block (base image) in the first image information and a predetermined image block (reference image) in the second image information. The degree of correlation in the pattern matching, for example, can be obtained through an evaluation function SAD (sum of absolute difference), which is the sum of the differences (absolute values) in luminance of the pixels between the base image and the reference image. Here, when a calculation block size of a small region is set to m×n pixels, SAD can be obtained through Expression 1.

$$SAD = \sum_{i=0}^{m-1} \sum_{j=0}^{n-1} |I0(x+i, y+j) - I1(x+dx+i, y+j)| \qquad (1)$$

Figure 9:
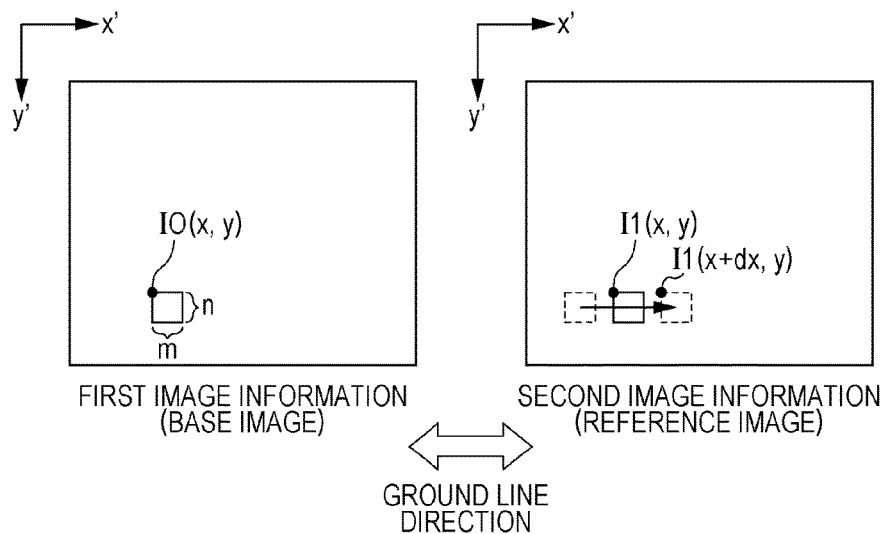
FIG. 9 is an illustration for describing a SAD calculation according to the first embodiment of the present disclosure.

In Expression 1, x and y represent coordinates on the imaging surface, and I0 and I1 represent, respectively, the luminance value of the base image and the luminance value of the reference image at the coordinates indicated in the parentheses. FIG. 9 is an illustration for describing the SAD calculation. In the SAD calculation, calculations are carried out while shifting the position of a search block region in the reference image by dx in the direction of the ground line (H-direction indicated in FIG. 1 and so on), as illustrated in FIG. 9, relative to a base block region in the base image, and dx at which the SAD takes a minimum value is determined to be parallax Px. The SAD can be calculated for any given coordinates, and thus the parallax can be extracted for the entire regions within the imaging field of view. Regions may be restricted in a case in which the parallax of a specific object in the field of view is to be extracted. The second signal processing unit C2, for example, extracts the parallax Px in a region corresponding to a predetermined region of the object.

The control unit CS generates a focus control signal on the basis of the parallax Px. The control unit CS, for example, includes a memory that stores data indicating a relationship between the parallax of the lens optical system L obtained in advance and the focus position, and determines the focus position on the basis of the parallax Px in accordance with the stored data. In addition, the control unit CS generates a focus control signal for moving the lens L2 of the lens optical system L to the determined focus position.

The lens actuation unit LD receives a focus control signal, and actuates the lens L2 in accordance with the focus control signal. Through this, the focus can be brought to a feature point of the object.

Fourth Embodiment

Figure 10:
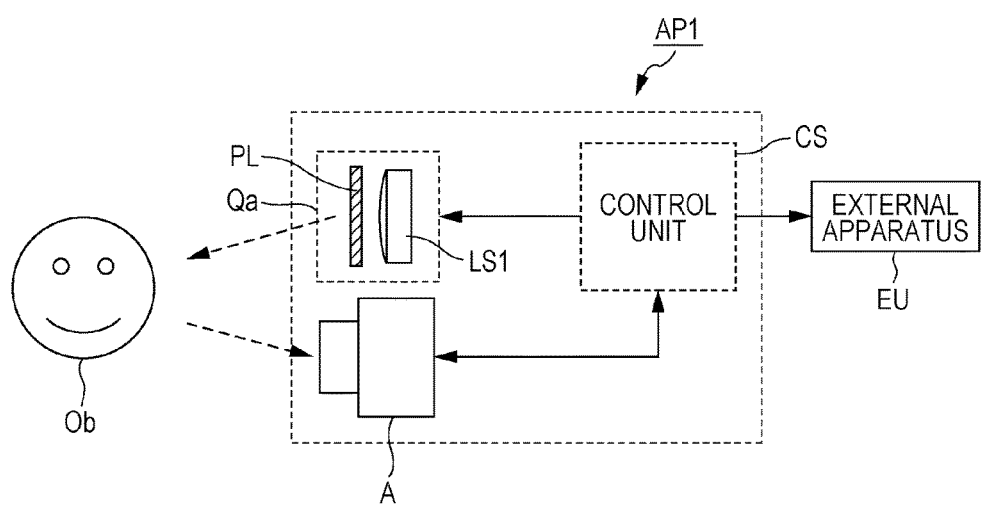
FIG. 10 is a schematic diagram illustrating an imaging system according to a fourth embodiment of the present disclosure.

A fourth embodiment differs from the first, second, and third embodiments in that a polarized illuminator is provided. FIG. 10 is a schematic diagram illustrating an imaging system AP1 according to the fourth embodiment. The imaging system AP1 according to the present embodiment includes, for example, the imaging apparatus A of the first embodiment, a polarized illuminator Qa, and a control unit CS. The control unit CS controls a timing at which the polarized illuminator Qa is lit and a timing at which the imaging apparatus A captures an image. In addition, the control unit CS receives image information from the imaging apparatus A, and outputs the image information to an external apparatus EU. The control unit CS may be constituted by an electronic circuit and so on, or may be constituted by a calculation device, a memory, and software. The polarized illuminator Qa includes a light source LS1 that emits visible light, and a polarization filter PL. The polarization filter PL includes a second polarization axis that is orthogonal to the polarization axis of the first optical region D1 of the imaging apparatus A. In addition, the control unit CS controls the imaging apparatus A and the polarized illuminator Qa, and controls input and output of data to and from the external apparatus EU. The external apparatus EU, for example, is a monitor that displays an image outputted from the imaging system AP1, or a personal computer that processes the image.

Light emitted from the light source LS1 passes through the polarization filter PL and reaches an object Ob. The polarization filter PL primarily transmits light that vibrates in the direction parallel to the second polarization axis, and absorbs most of light that vibrates in other directions (e.g., light that vibrates in the direction orthogonal to the second polarization axis). Thus, the polarized illuminator Qa irradiates the object Ob only with polarized light that vibrates in the direction of the second polarization axis.

The object Ob, for example, is a living body, such as facial skin of a person. The present embodiment will be described with facial skin of a person serving as the object Ob. Light that has reached the facial skin (object Ob) includes a component that is reflected and a component that is absorbed. The imaging apparatus A captures an image of the light component that is reflected. The light that is reflected by the facial skin includes a component that is reflected by the surface of the facial skin, and a component that enters into the facial skin, is scattered repeatedly, and is emitted from the facial skin at a position different from its point of entry into the facial skin.

The light that is reflected by the surface of the facial skin is further divided into a component that is specularly reflected and a component that is diffusely reflected. The component that is specularly reflected by the facial skin retains its polarization. Meanwhile, the component that is diffusely reflected by the facial skin and the component that enters into the facial skin and is emitted from a position different from the point of entry result in unpolarized light in which the polarization state is chaotic.

The polarization filter provided in the first optical region D1 of the imaging apparatus A has a polarization axis that is orthogonal to the polarization axis of the polarization filter PL in the polarized illuminator Qa, and thus blocks most of the light component that is specularly reflected by the facial skin. In addition, while the light that is diffusely reflected by the surface of the facial skin and the light that enters into the facial skin and is emitted from a position different from the point of entry are unpolarized, the polarization filter provided in the first optical region D1 of the imaging apparatus A transmits, among the aforementioned unpolarized light components, a light component that vibrates in the direction of the first polarization axis. In other words, image information obtained on the basis of the light that has passed through the first optical region D1 includes information on a light component that has been diffusely reflected by the surface of the facial skin and a light component that has entered into the facial skin and been emitted from a position different from the point of entry.

The aforementioned interior of the facial skin is an outer layer region of the facial skin, and melanin is present in a region of the outer layer region where a blotch is present. Light that has entered the outer layer of the facial skin is attenuated by melanin, and thus luminance of an image of a region corresponding to a blotch decreases. Therefore, the image generated on the basis of the light that has passed through the first optical region D1 results in an image in which most of the component that has been specularly reflected by the facial skin has been eliminated, or in other words, an image in which most of the shine on the facial skin has been eliminated, which makes it easier to observe the condition of blotches on the facial skin.

In the meantime, the second optical region D2 of the imaging apparatus A primarily transmits light that vibrates in the direction of the second polarization axis, and thus image information obtained by capturing the light that has passed through the second optical region D2 includes the light component that has been specularly reflected by the facial skin in a large amount. Therefore, the image generated on the basis of the light that has passed through the second optical region D2 clearly shows the shade caused by irregularities on the facial skin, and thus results in an image that makes it easier to recognize fine wrinkles and the textures in the skin.

Through the configuration described above, an image that makes it easier to recognize the condition of blotches can be obtained on the basis of the light that has passed through the first optical region D1 of the imaging apparatus A of the imaging system AP1; whereas, an image that makes it easier to recognize fine wrinkles and the textures in the skin can be obtained on the basis of the light that has passed through the second optical region D2.

In this manner, by using the imaging system AP1 according to the present embodiment, the conditions of the surface and the interior of a living body can be observed simultaneously. The imaging system AP1 can be applied to an apparatus for analyzing the skin condition or checking the condition of makeup in real time and also to a medical camera, such as an endoscope.

In addition, a configuration may be such that the above-described imaging system is mounted on a terminal, such as a personal computer, a smartphone, and a tablet terminal, that includes a display device, and is used as an electron mirror system.

Fifth Embodiment

A fifth embodiment corresponds to a configuration in which the imaging system AP1 of the fourth embodiment is applied to an electron mirror AP2. It is to be noted that any one of the imaging apparatuses A of the first through third embodiments may be used as the imaging apparatus A in the imaging system AP1.

Figure 11:
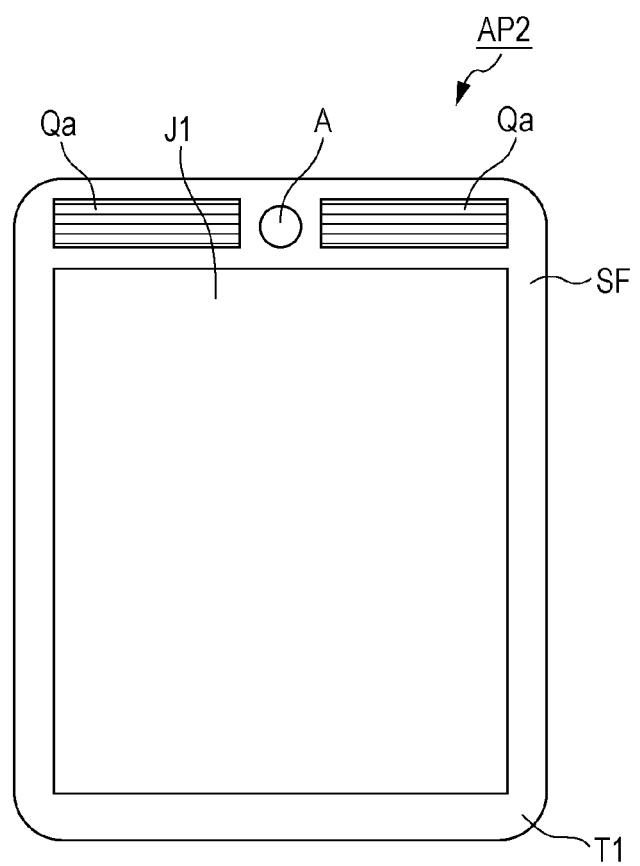
FIG. 11 is a front view of an electron mirror according to a fifth embodiment of the present disclosure.

FIG. 11 is a front view of the electron mirror AP2. The electron mirror AP2 includes a display J1, the imaging apparatus A, polarized illuminators Qa, and a housing T1 in which the display J1, the imaging apparatus A, and the polarized illuminators Qa are mounted. The housing T1 includes a principal surface SF and has a planar shape. The housing T1 includes a space having an opening in the principal surface SF, and the display J1 is housed in the space. As illustrated in FIG. 11, the principal surface SF of the housing T1 has a rectangular shape with rounded corners, and the imaging apparatus A is located at substantially the middle of one of the short sides of the principal surface SF. In addition, the two polarized illuminators Qa are provided along the short side of the principal surface SF so as to sandwich the imaging apparatus A. The display J1 is provided so as to be adjacent to the imaging apparatus A and the polarized illuminators Qa. In this manner, the display J1, the imaging apparatus A, and the polarized illuminators Qa are disposed along substantially the same plane on the principal surface SF in the electron mirror AP2. Through such a configuration, a thin electron mirror as in a tablet terminal can be implemented.

A white light-emitting diode (LED), for example, is used as a light source in the polarized illuminator Qa, and a polarization filter that primarily transmits light which vibrates in the direction of the first polarization axis is provided in the polarized illuminator Qa. As the polarized illuminator Qa configured in this manner irradiates the face of a person serving as an object with light, the imaging apparatus A can obtain, from light reflected by the person serving as the object, first color image information having information on polarized light that vibrates in the direction of the first polarization axis and second color image information having information on polarized light that vibrates in the direction of the second polarization axis simultaneously.

The image information obtained by the imaging apparatus A is displayed in real time on the display J1 in a horizontally inverted state. Furthermore, third unpolarized light color image information can be generated by adding and averaging the first color image information and the second color image information, and can also be displayed on the display J1.

Here, the configuration of the imaging apparatus A may be such that a transparent glass plate is provided in the optical region D1 and a polarization filter that transmits light which vibrates in the direction of the first polarization axis is provided in the optical region D2. Through such a configuration, first color image information having information on unpolarized light and second color image information having information on polarized light that vibrates in the direction of the first polarization axis can be obtained simultaneously.

Alternatively, the polarized illuminator Qa may be configured to emit light that vibrates in the direction of the first polarization axis. The configuration of the imaging apparatus A may be such that a transparent glass plate is provided in the optical region D1 and a polarization filter that transmits light which vibrates in the direction of the second polarization axis, which is orthogonal to the first polarization axis, is provided in the optical region D2. The lenticular lens K and the pixels in the color image sensor N may be disposed so as to hold the positional relationship as illustrated in FIG. 5B. Then, by providing the spectral filters X that transmit the spectrum of blue or cyan in the pixels P2, first image information having color information of unpolarized light and second image information having monochrome information of light that vibrates in the direction of the second polarization axis and that is in the spectrum of blue or the spectrum of cyan can be obtained simultaneously. The second image information results in an image in which most of the component that has been specularly reflected by the facial skin has been eliminated, or in other words, an image in which most of the shine on the facial skin has been eliminated, which makes it easier to observe the condition of blotches on the facial skin. As described in the fourth embodiment, light is attenuated by melanin, and thus luminance of an image of a region corresponding to a blotch decreases. In addition, melanin absorbs more light at shorter wavelengths, and thus a contrast created by blotches increases when an image is captured via a spectral filter for the spectrum of blue or cyan, making it easier to visualize. In addition, by using the spectrum of cyan, attenuation of light by a polarization filter can be reduced, and thus the sensitivity of the image can be increased as compared with a case in which the spectrum of blue is used. In addition, the first image information includes color information, and thus cyan image information of unpolarized light can be generated from blue image information and green image information. Therefore, by subtracting the second image information from the cyan image information of unpolarized light, third image information having information of polarized light that vibrates in the direction of the first polarization axis can be obtained. The third image information includes information of a light component that has been specularly reflected in a large amount, and thus clearly shows the shade caused by irregularities on the facial skin. Thus, an image that makes it easier to recognize fine wrinkles and the textures in the skin can be obtained.

By using the electron mirror AP2 configured in this manner, an image that makes it easier to recognize the condition of blotches, an image that makes it easier to recognize fine wrinkles and the textures in the facial skin, and a normal image can be obtained simultaneously, and the user serving as the object can check his or her own mirror image as if the user is looking into an ordinary mirror. A configuration may be such that the user can switch a displayed image among the aforementioned images as desired.

When the display J1 is constituted by a liquid crystal display, the object is also irradiated with light from the liquid crystal display. Therefore, a polarization filter provided on the front side of the liquid crystal display may have a polarization axis that coincides with the polarization axis of the polarized illuminator Qa. Through this, the polarization direction of the light from the liquid crystal display that reaches the object can be made to coincide with the polarization direction of the light from the polarized illuminator Qa.

In addition, as indicated by a dotted line in FIG. 1, the imaging apparatus A of the electron mirror AP2 may further include a third signal processing unit that generates information obtained by quantifying features of the skin of the object by using the first image information and the second image information, and may display the value obtained by quantifying the skin condition on the display J1. Through such a configuration, a skin analyzer system that allows the user to analyze the skin condition contactlessly while looking into a mirror can be implemented. For example, the imaging apparatus A may extract a portion of an image that corresponds to a blotch on the skin by using the first image information and the second image information, obtain the proportion of the area of the portion corresponding to the blotch, and display the result on the display J1. Alternatively, the imaging apparatus A may generate image data that indicates the portion corresponding to the blotch, superimpose the generated image on an image obtained from the first image information, an image obtained from the second image information, or an image obtained from the first image information and the second image information, and display the resulting image on the display J1.

The configuration of the skin analyzer system described above may be such that images are captured successively while turning on and off the polarized illuminator Qa and the skin condition is quantified by using differential images between the images captured when the polarized illuminator Qa is on and the images captured when the polarized illuminator Qa is off. Through such a configuration, a component of the ambient light, such as light from indoor lighting, other than the polarized illuminator Qa can be removed, and an influence of the ambient light, such as the light from the indoor lighting, can be eliminated. Thus, the accuracy in analyzing the skin can be increased.

In addition, a configuration may be such that, by using the imaging apparatus of the third embodiment as the imaging apparatus of the present embodiment, the parallax is extracted from the images of the user serving as the object and information for moving the position of the object on the basis of the parallax information is displayed on the display. For example, the imaging apparatus A includes the imaging unit IM, the first signal processing unit C1, and the second signal processing unit C2, and the second signal processing unit C2 calculates the parallax by using the first image information and the second image information, as described in the third embodiment. If the parallax is less than a predetermined value, the second signal processing unit C2 may generate information indicating that the distance to the object is large or information prompting the user to reduce the distance between the face and the electron mirror AP2. Meanwhile, if the parallax is greater than a predetermined value, the second signal processing unit C2 may generate information indicating that the distance to the object is small or information prompting the user to increase the distance between the face and the electron mirror AP2. These pieces of generated information may be displayed on the display J1. Alternatively, the electron mirror AP2 may include a sound generating device, and may present these pieces of information to the user through sound. Such a configuration makes it possible to capture an image of the user serving as the object always at a fixed distance, and thus the stability of the result of analyzing the skin condition can be maintained properly. In addition, an obtained result can be compared with an analysis result obtained previously, or can be checked against a database containing data from multiple people whose skin conditions have been captured under the same condition.

Sixth Embodiment

Figure 12:
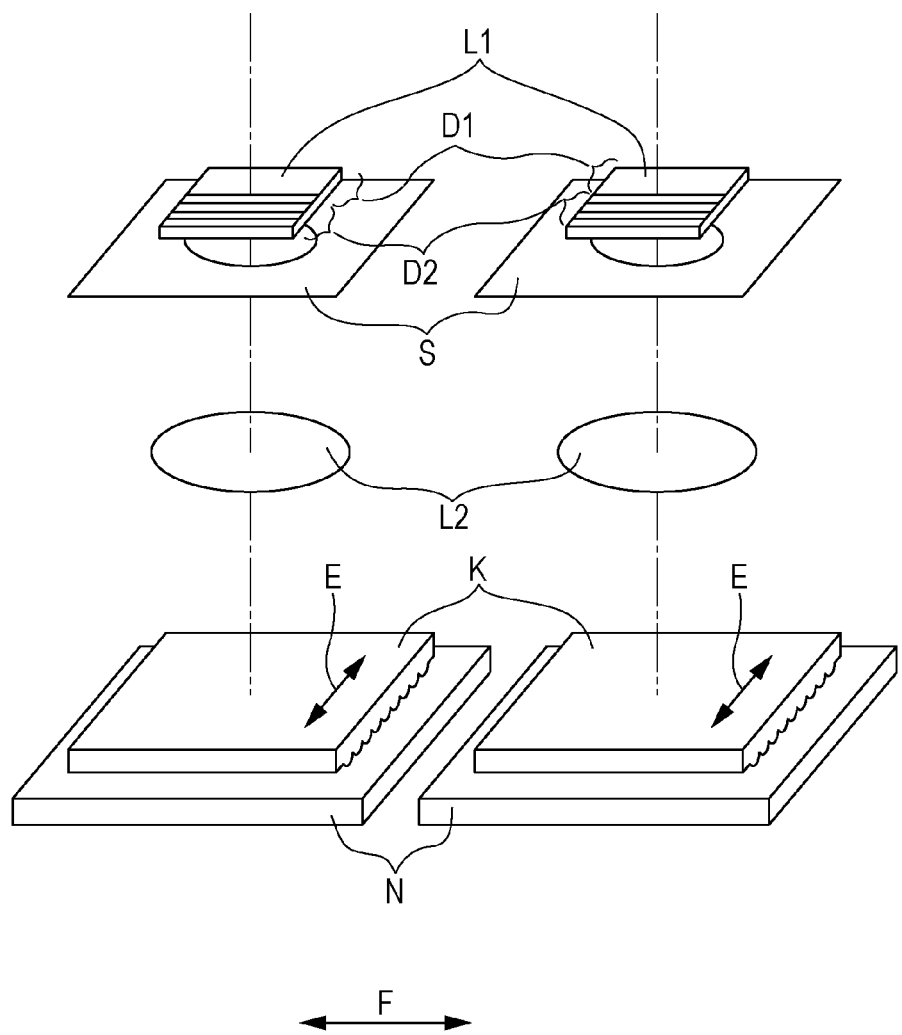
FIG. 12 is a schematic diagram of a ranging apparatus according to a sixth embodiment of the present disclosure.

A sixth embodiment corresponds to a ranging apparatus that includes a plurality of imaging apparatuses of the first embodiment or the second embodiment. FIG. 12 is a schematic diagram of the ranging apparatus that includes two imaging apparatuses. The reference characters indicated in FIG. 12 correspond to the respective reference characters indicated in FIG. 1. In the present embodiment, an array direction E in which the cylindrical lenses constituting the lenticular lenses of the respective imaging apparatuses are arrayed is orthogonal to a ground line direction F of the ranging apparatus. In the ranging apparatus, the parallax is extracted through pattern matching, and the distance to the object is calculated by using the extracted parallax through the principle of triangulation. Thus, as the array direction E in which the cylindrical lenses constituting the lenticular lenses are arrayed is orthogonal to the ground line direction F of the ranging apparatus, the resolution for parallax extraction can be increased as compared with a case in which the array direction E in which the cylindrical lenses constituting the lenticular lenses are arrayed is set to coincide with the ground line direction F.

Here, the configuration of the imaging apparatus A is such that a transparent glass plate is provided in the optical region D1 and a polarization filter that transmits light which vibrates in the direction of the first polarization axis is provided in the optical region D2. The lenticular lens K and the pixels in the color image sensor N are disposed so as to hold the positional relationship as illustrated in FIG. 5B, and the color filters X that transmit a spectrum of white (entire visible light spectrum) are provided on the pixels P2. Through such a configuration, first image information having color information can be generated by using luminance information of pixel groups constituted by the pixels P1, and second image information having monochrome polarized light information can be generated by using luminance information of pixel groups constituted by the pixels P2.

Such a configuration can be applied to an in-vehicle ranging camera. For example, in a case in which a lane is to be detected on a wet road, a first image that does not include information based on polarized light contains unwanted reflection light, which makes it difficult to recognize the lane. Meanwhile, unwanted reflection light can be reduced in a second image that has been obtained via a polarization filter, which makes it easier to recognize the lane. On the basis of such characteristics, the condition of the road surface can be estimated from the first image information that does not include information based on polarized light and the second image information that includes information based on polarized light, and an image that makes it easier to detect the lane can be generated by switching between the images or by combining the images on the basis of the estimated information. Through this, a ranging apparatus that facilitates detection of lanes can be implemented.

In addition, the configuration of the imaging apparatus A is such that a spectral filter that primarily transmits visible light is provided in the optical region D1 and another spectral filter that primarily transmits near-infrared light is provided in the optical region D2. The color filters X that transmit a spectrum of white (entire visible light spectrum) are provided on the pixels P2. Through such a configuration, first image information having color information can be generated by using luminance information of pixel groups constituted by the pixels P1, and monochrome image information of the near-infrared light can be generated by using luminance information of pixel groups constituted by the pixels P2.

Such a configuration can also be applied to an in-vehicle ranging camera. For example, the first image information having color information can be used during daytime, and while a near-infrared illuminator is additionally used at night, the monochrome image information of the near-infrared light can be used. Through this, an in-vehicle ranging apparatus that makes it possible to monitor the forward vision day or night can be implemented.

Seventh Embodiment

A seventh embodiment differs from the first embodiment in that an optical element L1p to be provided in the vicinity of the stop S has four regions and in that the plurality of pixels P are divided into four groups. Here, detailed descriptions of content in the present embodiment that is similar to the content in the first embodiment will be omitted.

Figure 13A:
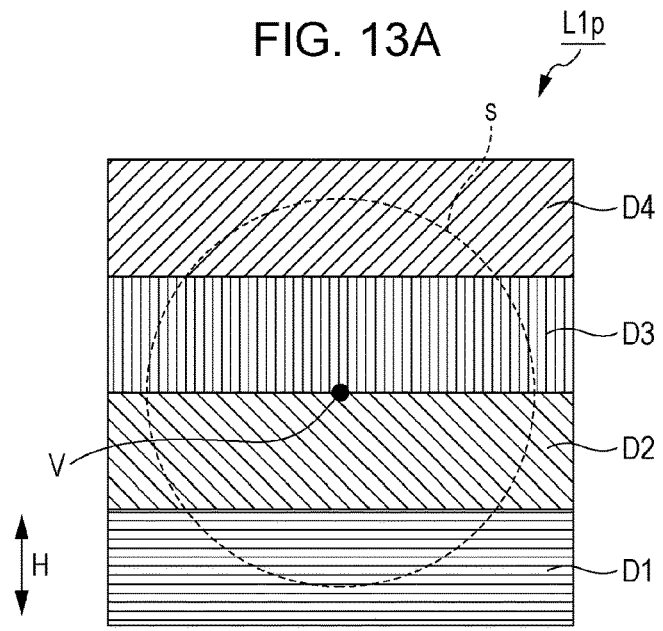
FIG. 13A is a front view, as viewed from an object, of first, second, third, and fourth optical regions of an optical element according to a seventh embodiment of the present disclosure.

As illustrated in FIG. 13A, the optical element L1p includes a first optical region D1, a second optical region D2, a third optical region D3, and a fourth optical region D4. The first optical region D1, the second optical region D2, the third optical region D3, and the fourth optical region D4 are arrayed in this order in the horizontal direction H (y-direction on the imaging surface Ni of the image sensor). A polarization filter that transmits light which vibrates in the direction of a first polarization axis (transmission axis) is provided in the first optical region D1. Another polarization filter that transmits light which vibrates in the direction of a second polarization axis (transmission axis), which is orthogonal to the first polarization axis, is provided in the second optical region D2. Another polarization filter that transmits light which vibrates in the direction of a third polarization axis, which differs from each of the first and second polarization axes by approximately 45°, is provided in the third optical region D3. The fourth optical region D4 is a region that transmits light which vibrates in the direction of a fourth polarization axis, which differs from each of the first and second polarization axes by approximately 45° and is orthogonal to the third polarization axis.

Figure 13B:
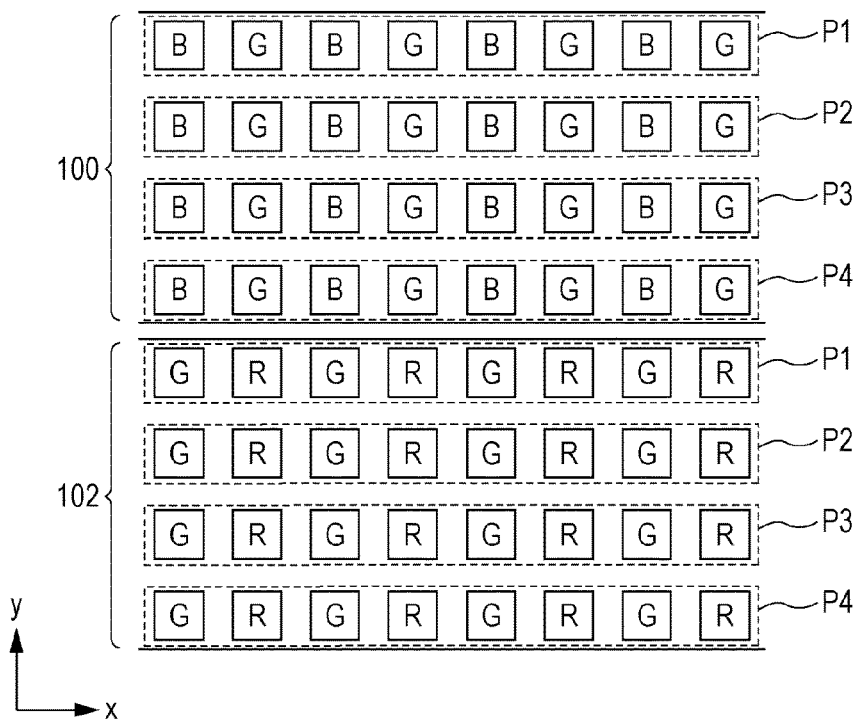
FIG. 13B illustrates a positional relationship between a lenticular lens and pixels in a color image sensor.

As illustrated in FIG. 13B, a plurality of pixels P1, a plurality of pixels P2, a plurality of pixels P3, and a plurality of pixels P4 are arrayed in respective rows in the x-direction. In the y-direction, rows of the pixels P1, rows of the pixels P2, rows of the pixels P3, and rows of the pixels P4 are disposed in this order in an alternating manner.

The lenticular lens K has a shape that is identical to the shape illustrated in FIG. 3. However, each cylindrical lens M1 is disposed so as to correspond to four rows of pixel groups in the imaging surface Ni: a row of a pixel group constituted by the pixels P1, a row of a pixel group constituted by the pixels P2, a row of a pixel group constituted by the pixels P3, and a row of a pixel group constituted by the pixels P4. Microlenses Ms are provided on the imaging surface Ni so as to cover the surfaces of the pixels P1, P2, P3, and P4.

In addition, the pixels P1, P2, P3, and P4 are disposed underneath the respective microlenses Ms and each include the photoelectric conversion unit EX, which is provided in the imaging surface Ni, and one of the color filter R (red), the color filter G (green), and the color filter B (blue), which are provided on the respective photoelectric conversion units EX. In the arrangement illustrated in FIG. 13B, the color filters R (red), G (green), and B (blue) are provided on the pixels P1, P2, P3, and P4. Specifically, in the imaging surface, the pixels P1, P2, P3, and P4 provided with either the color filter G (green) or the color filter R (red) are arrayed in an alternating manner in the x-direction in a unit region 102 corresponding to one of the cylindrical lenses M1 of the lenticular lens K, and the pixels P1, P2, P3, and P4 provided with either the color filter B (blue) or the color filter G (green) are arrayed in an alternating manner in the x-direction in a unit region 100 that is adjacent to the unit region 102 in the y-direction and that corresponds to another one of the cylindrical lenses M1.

Each cylindrical lens M1 in the lenticular lens directs light that has passed through the first optical region D1 to a plurality of pixels P1 in a corresponding unit region, directs light that has passed through the second optical region D2 to a plurality of pixels P2 in a corresponding unit region, directs light that has passed through the third optical region D3 to a plurality of pixels P3 in a corresponding unit region, and directs light that has passed through the fourth optical region D4 to a plurality of pixels P4 in a corresponding unit region.

Therefore, when one looks at only the rows of pixel groups constituted by the pixels P1, a row of a pixel group constituted by the pixels provided with either the color filter B (blue) or the color filter G (green) within the unit region 100 and a row of a pixel group constituted by the pixels provided with either the color filter G (green) or the color filter R (red) within the unit region 102 are arrayed in an alternating manner. In a similar manner, when one looks at only the rows of pixel groups constituted by the respective pixels P2, P3, and P4, a row of a pixel group constituted by the pixels provided with either the color filter B (blue) or the color filter G (green) within the unit region 100 and a row of a pixel group constituted by the pixels provided with either the color filter G (green) or the color filter R (red) within the unit region 102 are arrayed in an alternating manner. Accordingly, even if images are formed on the basis of the rows of pixel groups constituted by the respective pixels P1, P2, P3, and P4, each of the resulting images includes pixel signals corresponding to luminance values obtained from pixels provided with the color filters R, G, B. Thus, a color image is obtained in each case.

Through the configuration described above, first color image information having information of polarized light that vibrates in the direction of the first polarization axis, second color image information having information of polarized light that vibrates in the direction of the second polarization axis, which is orthogonal to the first polarization axis, third color image information having information of polarized light that vibrates in the direction of the third polarization axis, and fourth color image information having information of polarized light that vibrates in the direction of the fourth polarization axis can be obtained simultaneously by using the luminance information of the pixel groups constituted by the respective pixels P1, P2, P3, and P4.

Although the optical regions D1, D2, D3, and D4 of the optical element L1p are constituted by respective polarization filters having different polarization axes in the present embodiment, a configuration may be such that a transparent glass plate is provided in the optical region D1 and polarization filters having different polarization axes are provided in the respective optical regions D2, D3, and D4. Alternatively, a configuration may be such that no element is provided in the optical region D1 and polarization filters having different polarization axes are provided in the respective optical regions D2, D3, and D4.

Through such a configuration, it is possible to simultaneously obtain first color image information having information on unpolarized light by using the luminance information of the pixels P1 and second through fourth color image information having information on different polarization axes by using the luminance information of the pixels P1, P2, P3, and P4.

Figure 14A:
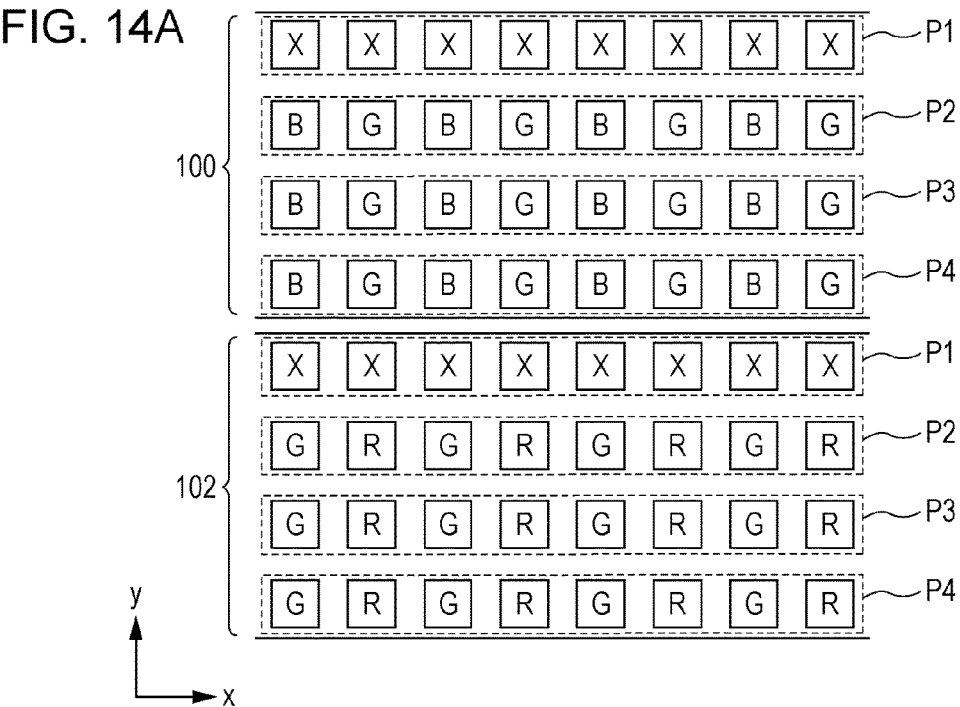
FIG. 14A illustrates a positional relationship between a lenticular lens and pixels in a color image sensor according to a modification of the seventh embodiment.
Figure 14B:
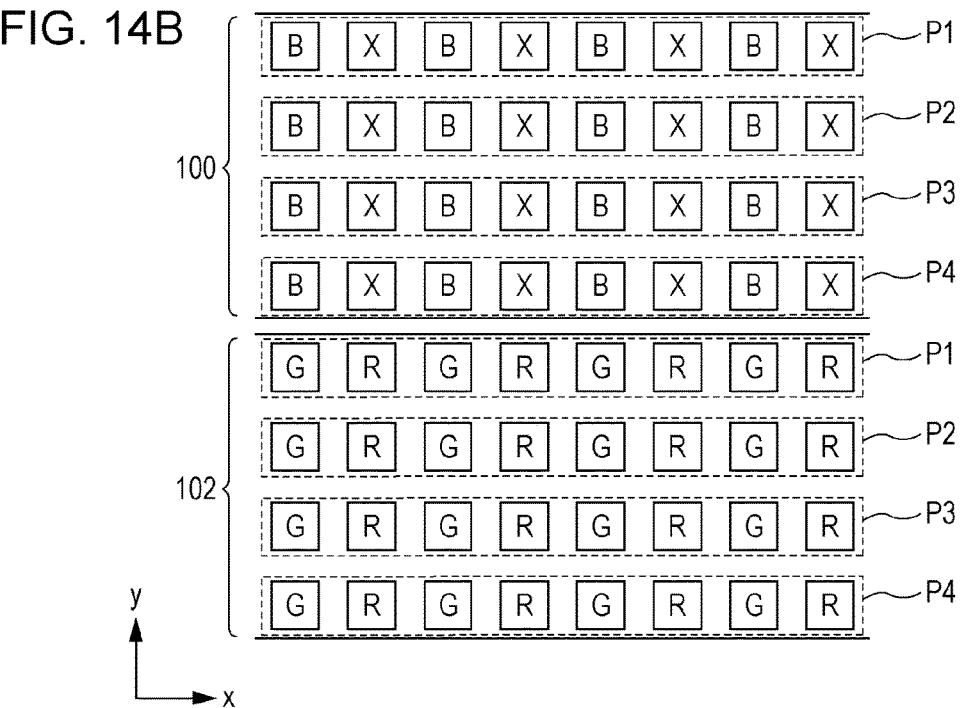
FIG. 14B illustrates a positional relationship between a lenticular lens and pixels in a color image sensor according to another modification of the seventh embodiment.

In addition, although the color filters R (red), G (green), and B (blue) are provided in the image sensor in the present embodiment, a different configuration of color filters may be employed. For example, as illustrated in FIGS. 14A and 14B, color filters R (red), G (green), B (blue), and X (color in any given spectrum) may be provided in the image sensor. In the case of the configuration illustrated in FIG. 14A, for example, the color in any given spectrum is a color in a spectrum of white (entire visible light spectrum), a spectrum of a complementary color, such as cyan, or a spectrum of non-visible light, such as near-infrared light or near-ultraviolet light. Through such a configuration, additional piece of spectral information can be used when images based on the two polarization axes are obtained simultaneously or when image information based on polarized light and image information based on unpolarized light are obtained simultaneously. In addition, in the case of the configuration illustrated in FIG. 14B, the color X in any given spectrum may be set to a color in any one of the spectra of R (red), G (green), and B (blue), a spectrum of white (visible light), a spectrum of a complementary color, such as cyan, or a spectrum of non-visible light, such as near-infrared light or near-ultraviolet light. Through such a configuration, the pixels P1 are reserved for image information only in a predetermined spectrum, and thus the resolution of image information corresponding to the information on the optical region D1 can be increased.

Eighth Embodiment

An eighth embodiment differs from the seventh embodiment in terms of the arrangement of the first optical region D1, the second optical region D2, the third optical region D3, and the fourth optical region D4 along a plane that is orthogonal to the optical axis, differs in terms of the arrangement of the plurality of pixels P1, P2, P3, and P4, and differs in that a microlens array is used in place of the lenticular lens. Here, detailed descriptions of content in the present embodiment that is similar to the content in the seventh embodiment will be omitted.

Figure 15A:
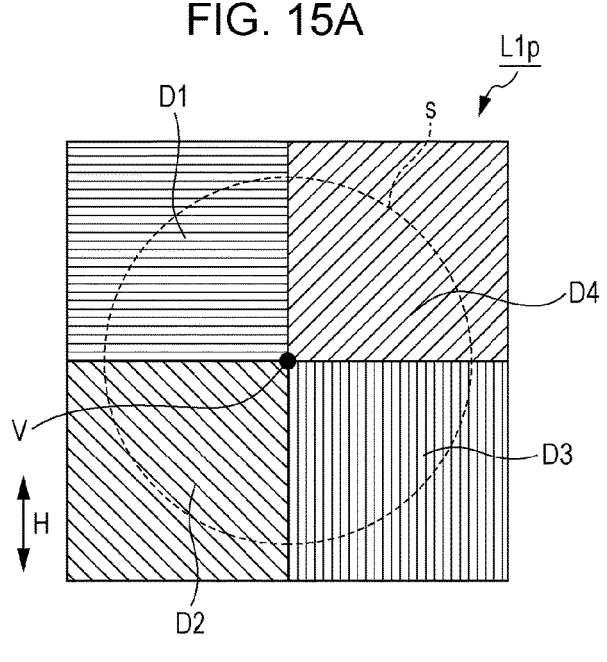
FIG. 15A is a front view, as viewed from an object, of first, second, third, and fourth optical regions of an optical element according to an eighth embodiment of the present disclosure.

As illustrated in FIG. 15A, an optical element L1p includes a first optical region D1, a second optical region D2, a third optical region D3, and a fourth optical region D4. The first optical region D1, the second optical region D2, the third optical region D3, and the fourth optical region D4 are four regions that are divided by a boundary that passes through the optical axis V and that is parallel to the horizontal direction H (y-direction on the imaging surface Ni of the image sensor) and another boundary that passes through the optical axis V and that is orthogonal to the horizontal direction H. A polarization filter that transmits light which vibrates in the direction of a first polarization axis (transmission axis) is provided in the first optical region D1. Another polarization filter that transmits light which vibrates in the direction of a second polarization axis (transmission axis), which is orthogonal to the first polarization axis, is provided in the second optical region D2. Another polarization filter that transmits light which vibrates in the direction of a third polarization axis, which differs from each of the first and second polarization axes by approximately 45°, is provided in the third optical region D3. The fourth optical region D4 is a region that transmits light which vibrates in the direction of a fourth polarization axis, which differs from each of the first and second polarization axes by approximately 45° and is orthogonal to the third polarization axis.

Figure 15B:
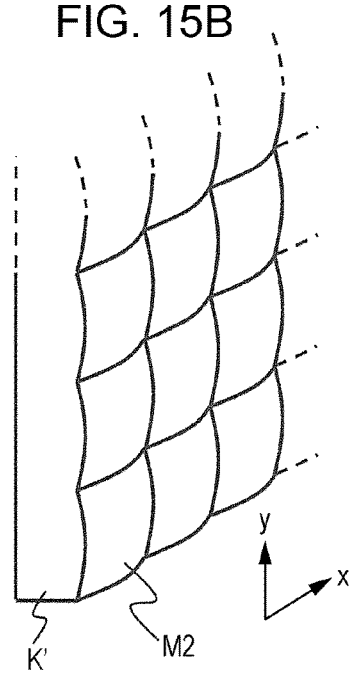
FIG. 15B is a perspective view of a microlens array.

FIG. 15B is a perspective view illustrating a microlens array K'. The microlens array K' includes a plurality of microlenses M2 that are arrayed in the x-direction and the y-direction. The section (section along a direction that is orthogonal to the x-direction and the y-direction) of each microlens M2 has a curve that protrudes toward the color image sensor N. The microlenses M2 are disposed such that each microlens M2 corresponds, among the plurality of pixels arrayed in the x-direction and the y-direction in the imaging surface Ni of the color image sensor N, to a total of 16 pixels in a unit region that are arranged in a matrix of four pixels in the x-direction and four pixels in the y-direction.

Figure 15C:
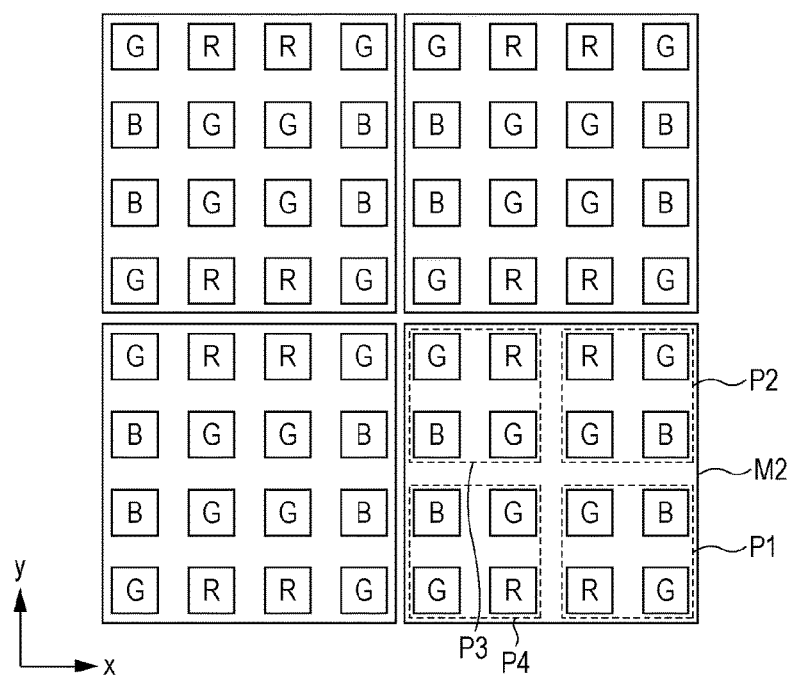
FIG. 15C illustrates a positional relationship between microlenses and pixels in a color image sensor.

As illustrated in FIG. 15C, the plurality of pixels arrayed in the imaging surface Ni include a plurality of pixels P1, a plurality of pixels P2, a plurality of pixels P3, and a plurality of pixels P4 that each include a color pixel group constituted by a set of four pixels that are arrayed in a matrix of two pixels in the x-direction and two pixels in the y-direction.

The color pixel groups include the photoelectric conversion units EX, which are provided in the imaging surface Ni, and the color filter R (red), the color filter G (green), and the color filter B (blue), which are provided on the respective photoelectric conversion units EX. As illustrated in FIG. 15C, in the present embodiment, for example, the color pixel groups in each of which a color filter R (red), a color filter B (blue), and two color filters G (green) are disposed are arrayed in the x-direction and the y-direction, and the color filters are disposed in a Bayer array.

Each microlens M2 in the microlens array K' directs light that has passed through the first optical region D1 to a color pixel group constituted by the pixels P1 in a unit region (region containing the 16 pixels enclosed by a solid line in FIG. 15C) corresponding to the microlens M2, directs light that has passed through the second optical region D2 to a color pixel group constituted by the plurality of pixels P2 in a unit region corresponding to the microlens M2, directs light that has passed through the third optical region D3 to a color pixel group constituted by the plurality of pixels P3 in a unit region corresponding to the microlens M2, and directs light that has passed through the fourth optical region D4 to a color pixel group constituted by the plurality of pixels P4 in a unit region corresponding to the microlens M2.

Therefore, light beams that have passed through the first optical region D1, the second optical region D2, the third optical region D3, and the fourth optical region D4 are detected, respectively, by the pixels P1, P2, P3, and P4, and the pixels P1, P2, P3, and P4 can output respective pixel signals corresponding to the luminance values obtained from the R, G, and B pixels in the respective unit regions. Accordingly, the light beams that have passed through the first optical region D1, the second optical region D2, the third optical region D3, and the fourth optical region D4 can be obtained in the form of respective color images.

Through the configuration described above, first color image information having information of polarized light that vibrates in the direction of the first polarization axis, second color image information having information on polarized light that vibrates in the direction of the second polarization axis, which is orthogonal to the first polarization axis, third color image information having information of polarized light that vibrates in the direction of the third polarization axis, and fourth color image information having information of polarized light that vibrates in the direction of the fourth polarization axis can be obtained simultaneously by using the luminance information of the pixel groups constituted by the pixels P1, the pixel groups constituted by the pixels P2, the pixel groups constituted by the pixels P3, and the pixel groups constituted by the pixels P4.

Although the optical regions D1, D2, D3, and D4 of the optical element L1p are constituted by polarization filters having different polarization axes in the present embodiment, a configuration may be such that a transparent glass plate is provided in the optical region D1 and polarization filters having different polarization axes are provided in the respective optical regions D2, D3, and D4. Alternatively, a configuration may be such that no element is provided in the optical region D1 and polarization filters having different polarization axes are provided in the respective optical regions D2, D3, and D4.

Through such a configuration, it is possible to simultaneously obtain first color image information having information on unpolarized light by using the luminance information of the pixels P1 and second through fourth color image information having information on different polarization axes by using the luminance information of the pixels P1, P2, P3, and P4.

Figure 16A:
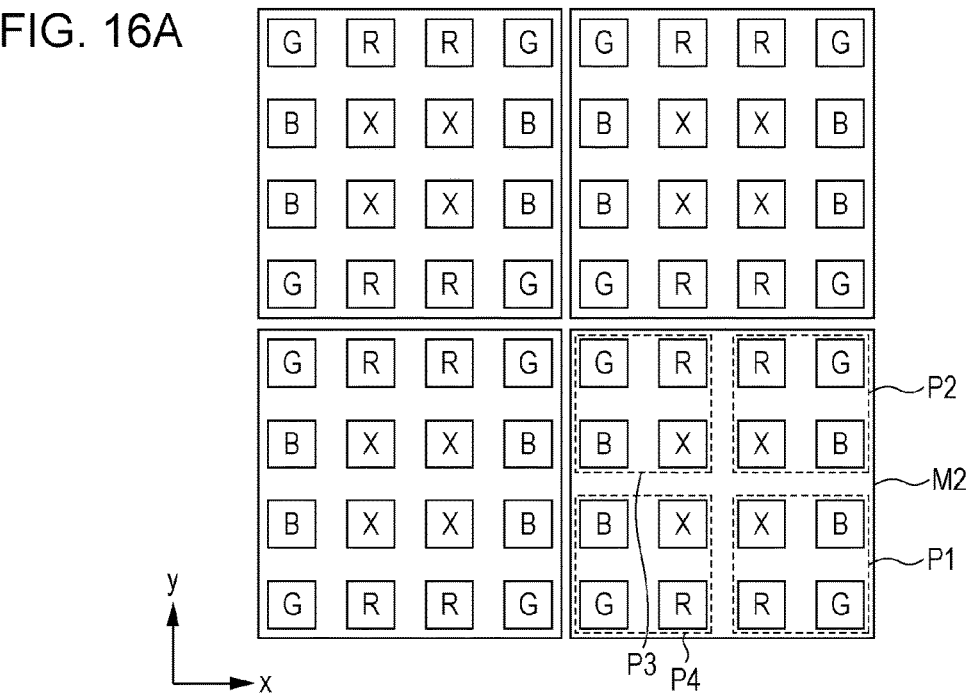
FIG. 16A illustrates a positional relationship between microlenses and pixels in a color image sensor according to a modification of the eighth embodiment.
Figure 16B:
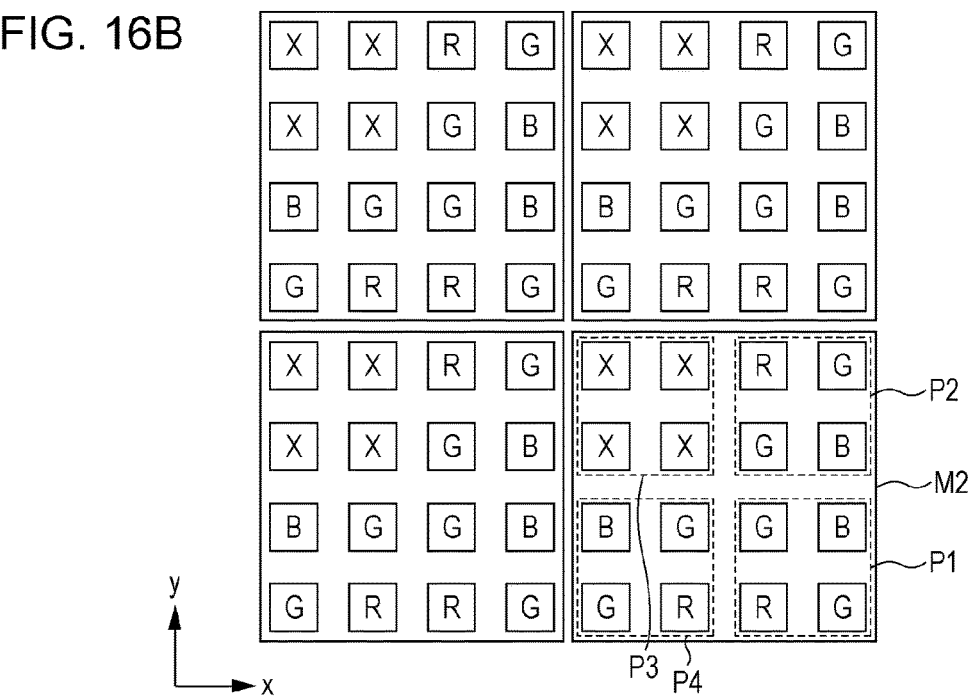
FIG. 16B illustrates a positional relationship between microlenses and pixels in a color image sensor according to another modification of the eighth embodiment.

In addition, although the color filters R (red), G (green), and B (blue) are provided in the image sensor in the present embodiment, a different configuration of color filters may be employed. For example, as illustrated in FIGS. 16A and 16B, the color pixel groups in the imaging surface may include pixels on which the color filters R (red), G (green), B (blue), and X (color in any given spectrum) are provided. In the case of the configuration illustrated in FIG. 16A, for example, the color in any given spectrum is a color in a spectrum of white (entire visible light spectrum), a spectrum of a complementary color, such as cyan, or a spectrum of non-visible light, such as near-infrared light or near-ultraviolet light. Through such a configuration, additional piece of spectral information can be used when images based on two polarization axes are obtained simultaneously or when image information based on polarized light and image information based on unpolarized light are obtained simultaneously. In addition, although the color filters are disposed in the same pattern among the color pixel groups constituted by the pixels P1, the color pixel groups constituted by the pixels P2, the color pixel groups constituted by the pixels P3, and the color pixel groups constituted by the pixels P4 in FIG. 15C, the arrangement of the color filters may differ among the color pixel groups as illustrated in FIG. 16A. In FIG. 16A, the color filters are arranged in each color pixel group in such a manner that the color filters X (color in any given spectrum) from the four color pixel groups within a unit region are located so as to be adjacent in the x-direction and in the y-direction.

In addition, although the pixel groups constituted by the respective pixels P1, P2, P3, and P4 within a unit region are each a color pixel group in the pixel array illustrated in FIG. 15C, a pixel group constituted by the pixels P1, P2, P3, or P4 within a unit region may include only one type of the color filters R (red), G (green), B (blue), and X (color in any given spectrum). For example, in the pixel array illustrated in FIG. 16B, the four pixels in each pixel group constituted by the pixels P3 include only the color filters X (color in any given spectrum). The color X, for example, may be a color in a spectrum of white (visible light), a spectrum of a complementary color, such as cyan, or a spectrum of non-visible light, such as near-infrared light or near-ultraviolet light. Through such a configuration, the pixels P1 are reserved for image information only in a predetermined spectrum, and thus the resolution of image information corresponding to the information of the optical region D1 can be increased.

Ninth Embodiment

A ninth embodiment differs from the first through eighth embodiments in that a third signal processing unit that generates an output image on the basis of image information generated by the first signal processing unit is provided.

An optical element L1 of an imaging apparatus according to the present embodiment includes an optical region in which a polarization filter is not provided and another optical region in which a polarization filter that transmits polarized light which vibrates in a predetermined direction is provided. In this case, color image information having information of unpolarized light and color image information having information of polarized light that vibrates in the predetermined direction can be obtained simultaneously.

Figure 17A:
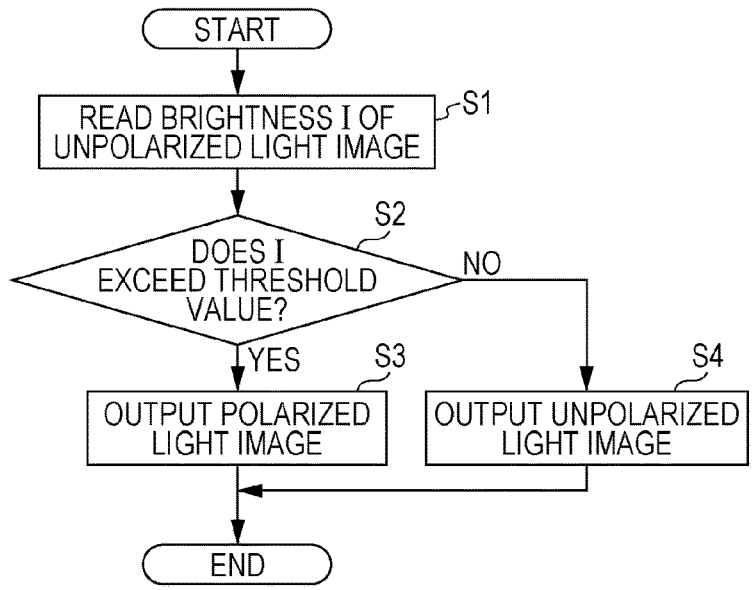
FIG. 17A is a flowchart for describing operations of a third signal processing unit according to a ninth embodiment of the present disclosure.

As illustrated in FIG. 17A, the third signal processing unit calculates brightness I of the image information of the unpolarized light (step S1), and compares the brightness I with a threshold value (step S2). If the brightness I exceeds the predetermined threshold value (step S3), the third signal processing unit may output polarized light image. Meanwhile, if the brightness I is equal to or less than the predetermined threshold value (step S4), the third signal processing unit may output unpolarized light image. The processes in step S1 through step S4 and the calculation of the brightness I can be carried out for the entire image or per pixel.

Through these processes, for example, in a case in which the imaging apparatus is disposed near the windshield of a vehicle so as to capture an image in the forward vision of the vehicle, it can be determined that the shooting environment is in daytime if the brightness I of the image exceeds the threshold value. Thus, by outputting a polarized light image, glare caused by reflected light from the windshield can be suppressed. Meanwhile, if the brightness I of the image is equal to or less than the threshold value, it can be determined that the shooting environment is in nighttime. Thus, by outputting an unpolarized light image, the sensitivity can be increased.

Figure 17B:
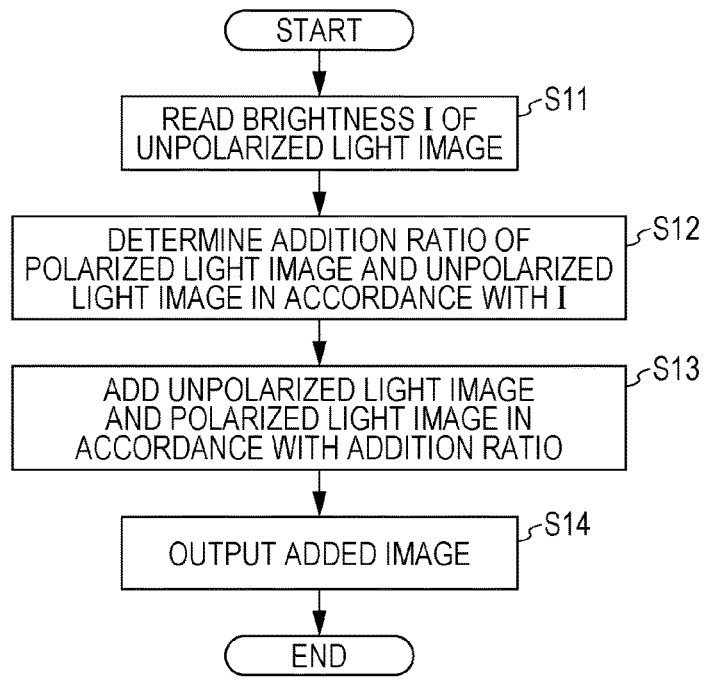
FIG. 17B is a flowchart for describing operations of the third signal processing unit according to the ninth embodiment of the present disclosure.

In addition, as illustrated in FIG. 17B, the third signal processing unit may read brightness I of the image information of the unpolarized light (step S11), determine an addition ratio of the polarized light image and the unpolarized light image in accordance with the brightness I (step S12), add the unpolarized light image and the polarized light image in accordance with the determined addition ratio (step S13), and output the result (step S14). The processes in step S11 through step S14 and the calculation of the brightness I can be carried out for the entire image or per pixel.

Through these processes, for example, in a case in which the imaging apparatus is disposed near the windshield of a vehicle so as to capture an image in the forward vision of the vehicle, an image in which glare caused by reflected light from the windshield is reduced can be outputted, and the sensitivity can be increased at the same time. As the front view of the vehicle is poorer at night or when it is raining, by increasing the ratio of the unpolarized light image, the sensitivity can be increased.

Tenth Embodiment

A tenth embodiment is implemented in a mode in which the imaging apparatus according to any one of the first through ninth embodiments is disposed near the windshield of a vehicle.

Figure 18A:
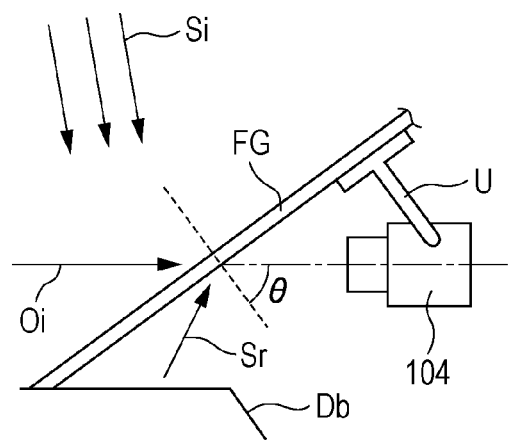
FIG. 18A is a schematic diagram illustrating a configuration of an imaging apparatus according to a tenth embodiment of the present disclosure.
Figure 18B:
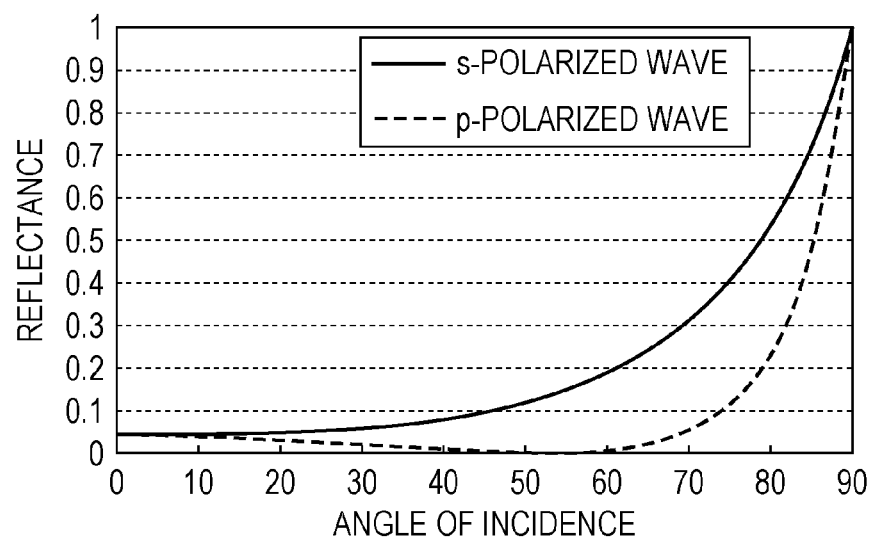
FIG. 18B illustrates a relationship between the angle of incidence and the reflectance of an S-polarized wave and a P-polarized wave.

As illustrated in FIG. 18A, light from the outside, such as the sun light Si, passes through a windshield FG and is incident on a dashboard Db. Having been reflected by the dashboard Db, the light is partially reflected by the windshield FG and the reflected light is incident on a camera 104. Through this, light from the dashboard Db appears in an image of an object Oi that is to be captured originally. The light from the dashboard Db can be prevented from appearing in the image by making an adjustment such that an angle θ formed by the direction of the optical axis of the camera 104 and the direction of normal to the surface of the windshield FG becomes equal to or less than 70°. FIG. 18B illustrates the relationship between the angle of incidence of light on the windshield FG and the reflectance. When the angle of incidence exceeds 70°, the reflectance of the P-polarized wave rises quickly. Thus, by setting the angle formed by the direction of the optical axis of the camera 104 and the direction of normal to the surface of the windshield FG to equal to or less than 70°, the angle of incidence of light on the windshield FG can be set to fall within a range in which the reflectance is low.

It is to be noted that the imaging apparatus according to any one of the first through tenth embodiments may be combined with another embodiment. For example, the imaging apparatus according to the seventh embodiment or the eighth embodiment may be combined with the third embodiment, the fourth embodiment, or the fifth embodiment. In the above embodiments, the first signal processing unit C1, the second signal processing unit C2, the third signal processing unit, the control unit CS and the lens actuation unit LD correspond to the first signal processor, the second signal processor, the third signal processor, the controller and the lens actuator in the imaging apparatus, the mirror system and the ranging apparatus of the present disclosure, respectively.

The imaging apparatus disclosed in the present application, for example, can be effectively used as a digital still camera, a digital video camera, an in-vehicle camera, a surveillance camera, a skin analyzer camera, an endoscope camera, and an imaging apparatus such as a capsule endoscope. In addition, the imaging apparatus disclosed in the present application can be applied to an imaging system, such as a microscope and an electron mirror.

What is claimed is:
1. An imaging apparatus, comprising:
a lens optical system;
a color image sensor that includes at least
 a plurality of first pixels on which light that has passed through the lens optical system is incident, and
 a plurality of second pixels on which light that has passed through the lens optical system is incident; and
a first optical element array disposed between the lens optical system and the color image sensor, wherein:
the lens optical system includes a plurality of optical regions,
the plurality of optical regions include a first optical region and a second optical region, the first and second optical regions differ in terms of at least one selected from the group of spectral transmittance characteristics and transmissive polarization characteristics,
the plurality of first pixels include respective spectral filters, the spectral filters having mutually different spectral transmittance characteristics,
the plurality of second pixels include respective spectral filters, the spectral filters having at least one type of spectral transmittance characteristics,
the first optical element array directs light that has passed through the first optical region to the plurality of first pixels and directs light that has passed through the second optical region to the plurality of second pixels,
the first optical element array is a first lenticular lens,
the first lenticular lens is provided on the color image sensor,
the plurality of first pixels include:
 spectral filters each having a spectral transmittance characteristic of red;
 spectral filters each having a spectral transmittance characteristic of green; and
 spectral filters each having a spectral transmittance characteristic of blue,
the plurality of second pixels include spectral filters each having a spectral transmittance characteristic of one of red, green, and blue,
the plurality of first pixels are arranged in first rows,
the plurality of second pixels are arranged in second rows, and
second pixels in one of the second rows include more spectral filters each having the spectral transmittance characteristic of the same color as the spectral transmittance characteristic of one of the spectral filters included in first pixels in one of the first rows than the first pixels in the one of the first rows.

2. The imaging apparatus according to claim 1,
wherein the color image sensor further includes
 a plurality of third pixels on which light that has passed through the lens optical system is incident, and
 a plurality of fourth pixels on which light that has passed through the lens optical system is incident,
wherein the plurality of optical regions in the lens optical system further include a third optical region and a fourth optical region,
wherein the first optical region, the second optical region, the third optical region, and the fourth optical region differ in terms of at least one selected from the group of spectral transmittance characteristics and transmissive polarization characteristics,
wherein the plurality of third pixels and the plurality of fourth pixels include respective spectral filters, the spectral filters having mutually different spectral transmittance characteristics, and
wherein the first optical element array directs light that has passed through the third optical region to the plurality of third pixels and directs light that has passed through the fourth optical region to the plurality of fourth pixels.

3. The imaging apparatus according to claim 1,
wherein the first optical region is constituted by a polarization filter that primarily transmits light which vibrates in a direction of a first polarization axis, and
wherein the second optical region is constituted by another polarization filter that primarily transmits light which vibrates in a direction of a second polarization axis, the second polarization axis being different from the first polarization axis.

4. The imaging apparatus according to claim 1,
wherein the first optical region transmits unpolarized light, and
wherein the second optical region is constituted by a polarization filter that primarily transmits light which vibrates in a direction of a predetermined polarization axis.

5. The imaging apparatus according to claim 1,
wherein the first optical region is constituted by a spectral filter that primarily transmits light in a visible-light spectrum, and
wherein the second optical region is constituted by another spectral filter that primarily transmits light in a non-visible-light spectrum.

6. The imaging apparatus according to claim 1, further comprising:
a second lenticular lens disposed between the first lenticular lens and the color image sensor,
wherein the first lenticular lens is provided on the color image sensor with the second lenticular lens provided therebetween.

7. The imaging apparatus according to claim 1, further comprising:
a microlens disposed between the first lenticular lens and the color image sensor,
wherein the first lenticular lens is provided on the color image sensor with the microlens provided therebetween.

8. The imaging apparatus according to claim 1, further comprising:
a first signal processor that, in operation, generates first image information and second image information on the basis of pixel signals obtained from the plurality of first pixels and the plurality of second pixels, respectively.

9. The imaging apparatus according to claim 8, further comprising:
a second signal processor that, in operation, generates parallax information of an object on the basis of the first image information and the second image information;
a controller that, in operation, generates a focus control signal on the basis of the parallax information; and
a lens actuator,
wherein the lens optical system includes at least one lens movable along an optical axis of the lens optical system, and
wherein the lens actuator moves the lens along the optical axis on the basis of the focus control signal.

10. The imaging apparatus according to claim 8, further comprising:
a third signal processor,
wherein the third signal processor, in operation,
reads brightness of at least one selected from the group of the first image information and the second image information,
compares the brightness with a predetermined threshold value, and
outputs at least one selected from the group of the first image information and the second image information in accordance with a result of the comparison.

11. The imaging apparatus according to claim 8, further comprising:
a third signal processor,
wherein the third signal processor, in operation,
reads brightness of at least one selected from the group of the first image information and the second image information,
determines an addition ratio of the first image information and the second image information in accordance with the brightness,
generates an added image obtained by adding the first image information and the second image information in accordance with the addition ratio, and
outputs the added image.

12. An imaging system, comprising:
the imaging apparatus according to claim 1; and
a polarized illuminator that emits polarized light.

13. The imaging system according to claim 12, further comprising:
a display that, in operation, displays an image obtained by the imaging apparatus.

14. An electron mirror system, comprising:
the imaging apparatus according to claim 8; and
a display that, in operation, displays an image obtained by the imaging apparatus.

15. The electron mirror system according to claim 14, further comprising:
a polarized illuminator that emits polarized light,
wherein the imaging apparatus, the polarized illuminator, and the display are disposed along substantially the same plane.

16. The electron mirror system according to claim 14, further comprising:
a third signal processor that, in operation, generates information in which a feature of an object is quantified by using the first image information and the second image information,
wherein the display, in operation, further displays the quantified information.

17. An imaging system, comprising:
the imaging apparatus according to claim 5; and
one of a near-infrared illuminator and a near-ultraviolet illuminator.

18. A ranging apparatus, comprising:
a plurality of imaging apparatuses according to claim 1.

19. The imaging apparatus according to claim 1, wherein all of the spectral filters included in second pixels in the one of the second rows have the spectral transmittance characteristic of the same color.

20. An imaging apparatus, comprising:
a lens optical system;
a color image sensor that includes at least
a plurality of first pixels on which light that has passed through the lens optical system is incident, and
a plurality of second pixels on which light that has passed through the lens optical system is incident; and
a first optical element array disposed between the lens optical system and the color image sensor, wherein:
the lens optical system includes a plurality of optical regions,
the plurality of optical regions include a first optical region and a second optical region, the first and second optical regions differ in terms of at least one selected from the group of spectral transmittance characteristics and transmissive polarization characteristics, the plurality of first pixels include respective spectral filters, the spectral filters having mutually different spectral transmittance characteristics, the plurality of second pixels include respective spectral filters, the spectral filters having at least one type of spectral transmittance characteristics, the first optical element array directs light that has passed through the first optical region to the plurality of first pixels and directs light that has passed through the second optical region to the plurality of second pixels, the first optical element array is a first lenticular lens, the first lenticular lens is provided on the color image sensor, the plurality of first pixels include:
- a spectral filter having a spectral transmittance characteristic of red;
- a spectral filter having a spectral transmittance characteristic of green; and
- a spectral filter having a spectral transmittance characteristic of blue, the plurality of second pixels include spectral filters each having a spectral transmittance characteristic of a color other than red, green, and blue, the plurality of first pixels are arranged in first rows, the plurality of second pixels are arranged in second rows, and all of the spectral filters included in second pixels in one of the second rows have the spectral transmittance characteristic of the same color.

21. The imaging apparatus according to claim 20, wherein the first rows and the second rows are disposed in an alternating manner.

22. The imaging apparatus according to claim 20, wherein the plurality of second pixels include spectral filters each having a spectral transmittance characteristic of a visible color other than red, green, and blue.

* * * * *